United States Patent
Moriyama et al.

(10) Patent No.: US 8,497,898 B2
(45) Date of Patent: Jul. 30, 2013

(54) ENDOSCOPE SYSTEM AND LOW VISIBILITY DETERMINING METHOD

(75) Inventors: Hiroki Moriyama, Akishima (JP); Yoshitaka Umemoto, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/357,738

(22) Filed: Jan. 25, 2012

(65) Prior Publication Data

US 2012/0182409 A1 Jul. 19, 2012

Related U.S. Application Data

(63) Continuation of application No. PCT/JP2011/068626, filed on Aug. 17, 2011.

(30) Foreign Application Priority Data

Sep. 14, 2010 (JP) .................................. 2010-205896

(51) Int. Cl.
*H04N 7/18* (2006.01)

(52) U.S. Cl.
USPC .......................................................... 348/65

(58) Field of Classification Search
USPC .......................................................... 348/65
See application file for complete search history.

(56) References Cited

U.S. PATENT DOCUMENTS

| | | | |
|---|---|---|---|
| 2006/0184048 A1 | 8/2006 | Saadat | |
| 2007/0156021 A1* | 7/2007 | Morse et al. | 600/167 |
| 2007/0197865 A1 | 8/2007 | Miyake et al. | |
| 2008/0292154 A1 | 11/2008 | Nishimura et al. | |
| 2008/0303898 A1 | 12/2008 | Nishimura | |
| 2009/0088634 A1 | 4/2009 | Zhao et al. | |

FOREIGN PATENT DOCUMENTS

| | | |
|---|---|---|
| EP | 1 842 481 A1 | 10/2007 |
| EP | 2 014 219 A2 | 1/2009 |
| JP | 06-098854 | 4/1994 |
| JP | 08-336497 | 12/1996 |
| JP | 09-149876 | 6/1997 |
| JP | 09-266882 | 10/1997 |
| JP | 10-243919 | 9/1998 |

(Continued)

OTHER PUBLICATIONS

European Search report dated Jan. 4, 2013 from corresponding European Patent Application No. 11 82 4931.7.

*Primary Examiner* — David Czekaj
*Assistant Examiner* — Tracy Li
(74) *Attorney, Agent, or Firm* — Scully, Scott, Murphy & Presser, P.C.

(57) ABSTRACT

An endoscope system includes an image pickup section, provided in an endoscope, which performs image pickup, a determining section that determines whether a specific observation object exists inside an image pickup region of the image pickup section, a recognizing section that determines whether the specific observation object can be recognized as an image from the picked-up image in the image pickup region picked up by the image pickup section, a low visibility determination output section that determines, when the determining section determines that the specific observation object exists inside the image pickup region and the recognizing section cannot recognize the specific observation object as an image, that the image pickup section is in a low visibility condition and outputs a low visibility determination result, and an obstacle estimation section that estimates an obstacle or a type of obstacle which causes the low visibility according to the low visibility determination result.

10 Claims, 17 Drawing Sheets

FOREIGN PATENT DOCUMENTS

| | | |
|---|---|---|
| JP | 10-276974 | 10/1998 |
| JP | 11-309156 | 11/1999 |
| JP | 11-318909 | 11/1999 |
| JP | 2005-124756 | 5/2005 |
| JP | 2006-166939 | 6/2006 |
| JP | 2007-159738 | 6/2007 |
| JP | 2007-222238 | 9/2007 |
| JP | 2008-301968 | 12/2008 |
| JP | 2009-131466 | 6/2009 |

* cited by examiner

| | | POSITION DETERMINATION RESULT | |
|---|---|---|---|
| | | INSIDE IMAGE PICKUP REGION | OUTSIDE IMAGE PICKUP REGION |
| IMAGE RECOGNITION RESULT | IMAGE RECOGNITION POSSIBLE | GOOD VISIBILITY | OUTSIDE FIELD OF VIEW |
| | IMAGE RECOGNITION NOT POSSIBLE | LOW VISIBILITY | OUTSIDE FIELD OF VIEW |

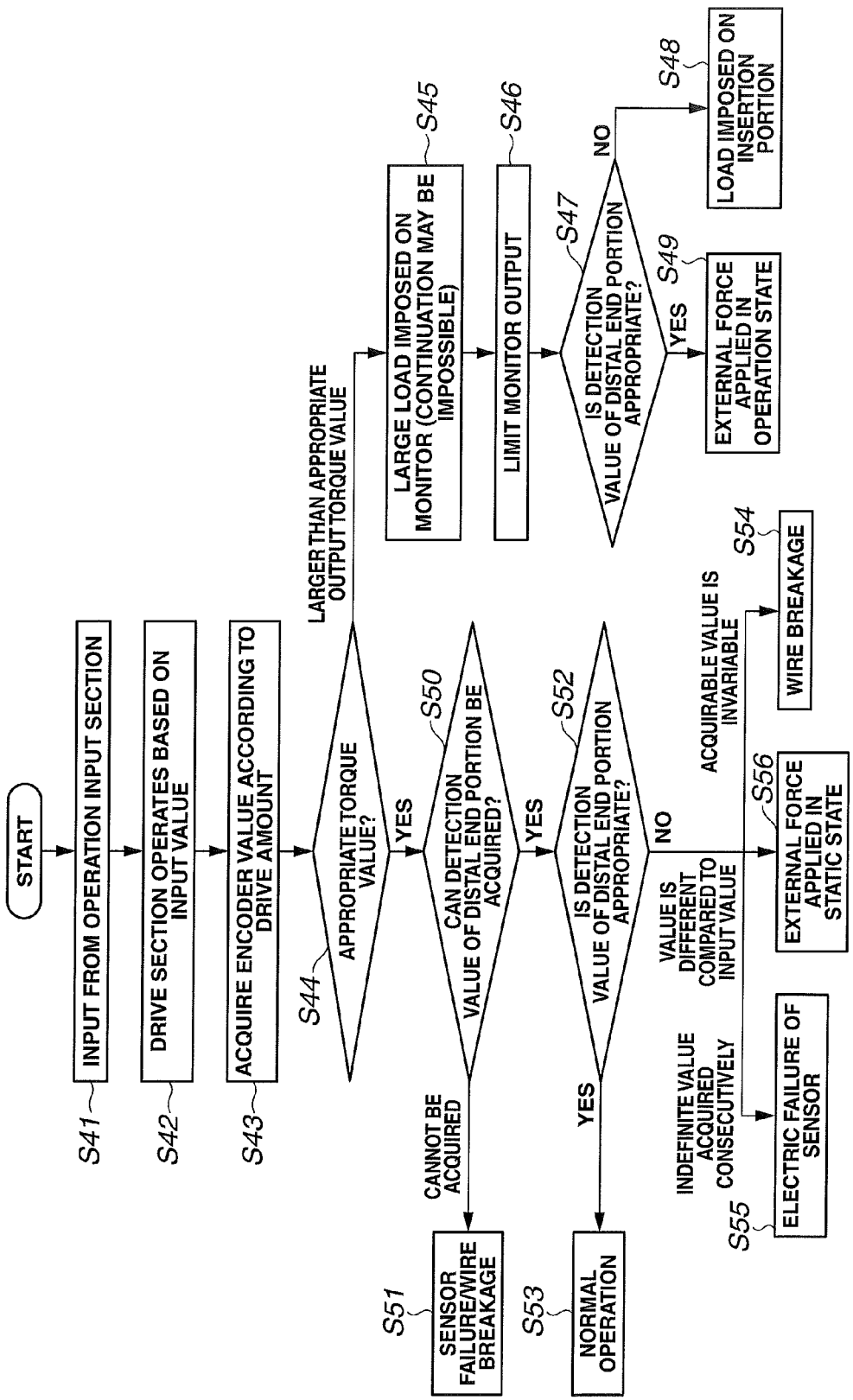

FIG.18

|  | STATUS | | | |
| --- | --- | --- | --- | --- |
|  | ACTIVE TREATMENT INSTRUMENT | PROCESSOR | ENERGY DEVICE | INSUFFLATOR |
| ACTIVE TREATMENT INSTRUMENT (TREATMENT MANIPULATOR) | STOPPED | CONTINUED | STOPPED | CONTINUED |
| PROCESSOR (IMAGING SECTION) | STOPPED | STOPPED | STOPPED | CONTINUED |
| ENERGY DEVICE (HIGH-FREQUENCY TREATMENT INSTRUMENT) | TEMPORARILY STOPPED | CONTINUED | STOPPED | CONTINUED |
| INSUFFLATOR | TEMPORARILY STOPPED | CONTINUED | STOPPED | CONTINUED |

…

ENDOSCOPE SYSTEM AND LOW VISIBILITY DETERMINING METHOD

CROSS REFERENCE TO RELATED APPLICATION

This application is a continuation application of PCT/JP2011/068626 filed on Aug. 17, 2011 and claims benefit of Japanese Application No. 2010-205896 filed in Japan on Sep. 14, 2010, the entire contents of which are incorporated herein by this reference.

BACKGROUND OF THE INVENTION

1. Field of the Invention

The present invention relates to an endoscope system and a low visibility determining method that performs image pickup using image pickup means of an endoscope and determines low visibility.

2. Description of the Related Art

In recent years, endoscopes provided with image pickup means are widely used for an observation and diagnosis or the like of diseased tissues. Furthermore, endoscopes are also widely used when conducting a surgical operation using a high-frequency treatment instrument making up a high-frequency electrocoagulation apparatus under observation with an endoscope.

Under observation with an endoscope, for example, a diseased tissue is subjected to a treatment such as electrocoagulation by capturing a treatment portion in the vicinity of a distal end portion of a high-frequency treatment instrument within an image pickup region of the image pickup means. Smoke or mist may be generated when conducting a treatment on the tissue.

Japanese Patent Application Laid-Open Publication No. 11-318909 as a first related art discloses a system provided with smoke detecting means for detecting smoke from an image obtained by image pickup means when conducting a treatment on high-frequency electrocoagulation using a high-frequency electrocoagulation apparatus under observation with a rigid endoscope for controlling pneumoperitoneal means to remove smoke.

Furthermore, Japanese Patent Application Laid-Open Publication No. 2007-159738 as a second related art discloses an endoscope system provided with determining means for determining whether a treatment section at a distal end portion of a treatment instrument is located in a first region set inside an image pickup region of image pickup means or a second region set around the first region from the image picked up by the image pickup means.

Furthermore, this second related art also discloses that a region where a treatment section is located is announced based on the determination result by the determining means and, when the treatment section is located in the second region, the treatment section is controlled so as to move to the first region.

SUMMARY OF THE INVENTION

An endoscope system according to an aspect of the present invention includes an image pickup section, provided in an endoscope, that performs image pickup, a determining section that determines whether or not a specific observation object exists inside an image pickup region of the image pickup section, a recognizing section that determines whether or not the specific observation object can be recognized as an image from the picked-up image in the image pickup region picked up by the image pickup section, a low visibility determination output section that determines, when the determining section determines that the specific observation object exists inside the image pickup region and the recognizing section cannot recognize the specific observation object as an image, that the image pickup section is in a low visibility condition and outputs a low visibility determination result, and an obstacle estimation section that estimates an obstacle or a type of obstacle which causes the low visibility according to the low visibility determination result.

A low visibility determining method according to an aspect of the present invention includes a display step of displaying an image of a site to be observed in a body cavity picked up by an image pickup section as an endoscope image, a treatment instrument position acquiring step of a position determining section acquiring a position of a distal end portion of a treatment instrument for conducting a treatment of the site to be observed, a position determining step of the position determining section determining whether or not the distal end portion of the treatment instrument is located inside an image pickup region as a region of the picked-up image, a recognizing step of an image recognizing section conducting image recognition as to whether or not the distal end portion of the treatment instrument can be recognized as an image of an interior of the image pickup region through image processing on the picked-up image, a low visibility determination outputting step of a low visibility determining section determining low visibility when the distal end portion of the treatment instrument is determined in the position determining step to be inside the image pickup region and the recognition result in the recognizing step shows that the distal end side of the treatment instrument cannot be recognized as an image inside the image pickup region and outputting a low visibility determination result, and an obstacle estimating step of an obstacle estimation section estimating, when the low visibility determination result is outputted in the low visibility determination outputting step, an obstacle or a type of obstacle that causes the low visibility.

BRIEF DESCRIPTION OF THE DRAWINGS

FIG. 17 is a flowchart illustrating processing contents in FIG. 16; and

FIG. 18 is a table illustrating examples where operation of each device in which an abnormal state is detected is continued or stopped.

DETAILED DESCRIPTION OF THE PREFERRED EMBODIMENTS

Hereinafter, embodiments of the present invention will be described with reference to the accompanying drawings.

First Embodiment

Figure 1:
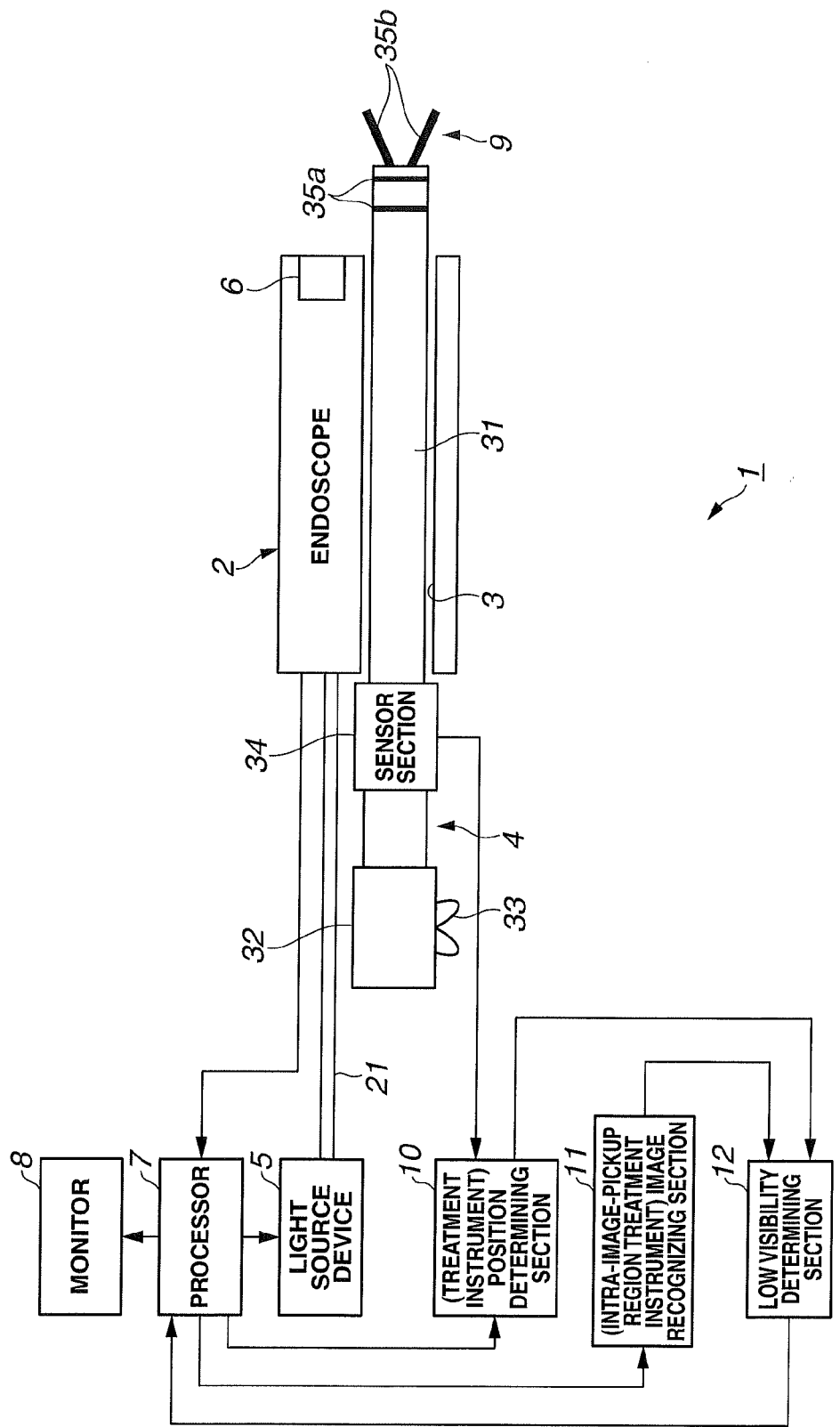
FIG. 1 is a configuration diagram illustrating an overall configuration of an endoscope system according to a first embodiment of the present invention.

As shown in FIG. 1, an endoscope system 1 according to a first embodiment of the present invention includes an endoscope 2 inserted into a body, a treatment instrument 4 inserted into a treatment instrument channel (simply abbreviated as "channel") 3 of the endoscope 2 and a light source device 5 that supplies illuminating light to the endoscope 2.

Furthermore, this endoscope system 1 includes a processor 7 as signal processing means for performing signal processing with respect to an image pickup section 6 as image pickup means provided in the endoscope 2 and a monitor 8 as display means for displaying an endoscope image corresponding to an image signal generated by the processor 7.

The light source device 5 and the processor 7 may be connected together via a signal line and a light quantity of illuminating light from the light source device 5 may be adjusted by a brightness signal of the image signal from the processor 7.

Furthermore, this endoscope system 1 includes a treatment instrument position determining section (hereinafter simply abbreviated as "position determining section") 10 as determining means for determining whether or not a treatment section 9 provided at a distal end portion of the treatment instrument 4 that performs a treatment is located within an image pickup region where the image pickup section 6 can perform image pickup, namely, whether or not the distal end portion of the treatment instrument 4 (as a specific observation object) is located at a position within a field of view of the image pickup section 6.

Furthermore, this endoscope system 1 includes an intra-image-pickup-region treatment instrument image recognizing section (hereinafter simply abbreviated as "image recognizing section") 11 as recognizing means for determining whether or not the distal end portion of the treatment instrument 4 (as a specific observation object) can be recognized as an image from a picked-up image in the image pickup region by the image pickup section 6 or from an endoscope image (corresponding to the picked-up image in the image pickup region).

Furthermore, this endoscope system 1 includes a low visibility determining section 12 as low visibility determination outputting means for determining whether an image pickup state of the distal end portion of the treatment instrument by the current image pickup section 6 is a good visibility state or a low visibility state from information on the determination result by the position determining section 10 and information on the recognition result by the image recognizing section 11.

This low visibility determining section 12 outputs information on the determination result to the processor 7. The processor 7 displays the information on the determination result on the monitor 8 to announce it to a surgeon or the like. Therefore, this monitor 8 forms announcing means for announcing the information on the determination result to the surgeon or the like. When low visibility occurs, the user such as a surgeon can immediately grasp the state thereof according to the information displayed on the monitor 8. Instead of announcement by a display or in addition to announcement by display, announcing means that performs announcement acoustically using a buzzer, speaker or the like may also be provided.

FIG. 1 shows a configuration example in which the position determining section 10, the image recognizing section 11 and the low visibility determining section 12 are provided outside the processor 7, but a configuration may also be adopted in which, for example, the position determining section 10, the image recognizing section 11 and the low visibility determining section 12 are provided inside the processor 7.

Figure 2:
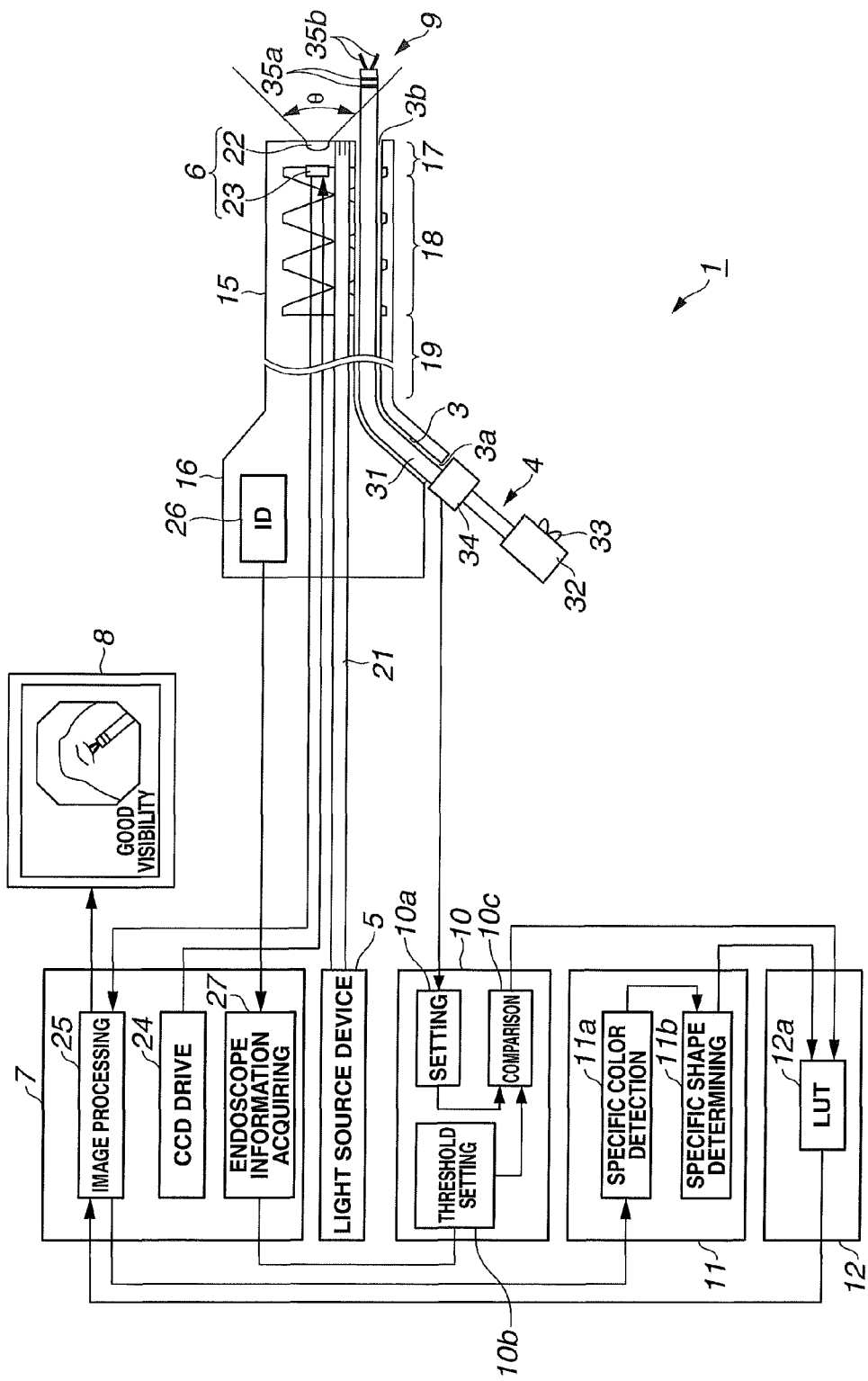
FIG. 2 is a diagram illustrating another more detailed configuration of the endoscope in FIG. 1.

FIG. 2 illustrates a more detailed configuration of the endoscope 2 or the like in FIG. 1. The endoscope 2 includes an elongated insertion portion 15 inserted into the body cavity and an operation section 16 provided at a rear end of the insertion portion 15. The insertion portion 15 includes a distal end portion 17 provided at a distal end thereof, a bendable bending portion 18 provided at a rear end of the distal end portion 17 and a flexible portion 19 extending from a rear end of the bending portion 18 to a front end of the operation section 16.

The bending portion 18 is configured by pivotably connecting a plurality of bending pieces and the surgeon can bend the bending portion 18 in a desired direction by operating a bending operation knob (not shown) provided at the operation section 16.

A light guide 21 that guides illuminating light is inserted into the insertion portion 15 and a proximal end of the light guide 21 is detachably connected to the light source device 5 outside the endoscope 2. Illuminating light generated by the light source device 5 is guided by the light guide 21.

A distal end of the light guide 21 is fixed to an illuminating window of the distal end portion 17 and the guided illuminating light is outputted from the illuminating window.

An objective lens 22 is attached to an observation window adjacent to the illuminating window and, for example, a charge coupled device (abbreviated as "CCD") 23 is arranged at its image forming position as an image pickup device.

The objective lens 22 forms an optical image of an object such as a diseased part in the body cavity illuminated with the illuminating light outputted from the illuminating window on an image pickup surface of the CCD 23. The CCD 23 photoelectrically converts the formed optical image. The objective lens 22 and the CCD 23 constitute the image pickup section 6 that picks up an image of the diseased part or the like in the body cavity.

As shown in FIG. 2, the objective lens 22 forms an optical image of an object within a predetermined range of field of view (indicated by a viewing angle θ) on the image pickup surface of the CCD 23. This viewing angle θ becomes an image pickup region (image pickup range) within which image pickup is possible.

The CCD 23 is connected to a CCD drive circuit 24 and an image processing circuit 25 of the processor 7 via signal lines passing through the insertion portion 15 and the operation section 16. The CCD drive circuit 24 generates a CCD drive signal and applies the CCD drive signal to the CCD 23.

Upon receiving the CCD drive signal applied, the CCD 23 outputs a photoelectrically converted signal as an image pickup signal picked up by the CCD 23 (of the image pickup section 6). This image pickup signal is subjected to image processing (video processing) by the image processing circuit 25 and an image signal is generated which can be displayed on the monitor 8. Upon receiving this image signal from the image processing circuit 25, the monitor 8 displays the picked-up image captured by the image pickup section 6 as an endoscope image.

Furthermore, the channel 3 is provided inside the insertion portion 15 of the endoscope and a rear end of the channel 3 is open as an insertion port 3a in the vicinity of the front end of the operation section 16 and a distal end of the channel 3 is open as a distal end opening (or port) 3b on a distal end face of the distal end portion 17.

The endoscope 2 is provided with an ID generation section 26 that generates specific information (ID information) containing information such as an image pickup characteristic of the image pickup section 6 provided in each endoscope 2 and an arrangement of the channel 3.

The ID information by the ID generation section 26 is referenced by an endoscope information acquiring circuit 27 provided in the processor 7 and the endoscope information acquiring circuit 27 acquires mainly information on the distal end portion 17 of the actually used endoscope 2 and particularly information on the arrangement of the image pickup region (viewing angle θ) of the image pickup section 6 and the distal end opening 3b of the channel 3 with reference to the ID information. It is also possible to acquire information on the length of the channel 3 in the endoscope 2 from the ID information.

The endoscope information acquiring circuit 27 generates determination information necessary to determine whether or not mainly the treatment section 9 of the distal end portion of the treatment instrument 4 comes to be observed (imaged) when the distal end side of the treatment instrument 4 protrudes (how much from the distal end face of the distal end portion 17) from the arrangement information on the distal end opening 3b of the channel 3 arranged in the periphery thereof at a viewing angle θ of the objective lens 22 that determines the image pickup region of the image pickup section 6. This determination information is outputted to the position determining section 10.

The configuration example in FIG. 2 shows a configuration in which the endoscope information acquiring circuit 27 is provided in the processor 7, but the endoscope information acquiring circuit 27 may be provided inside the position determining section 10. The treatment instrument 4 includes an elongated tubular member 31, an operation section 32 provided at a rear end thereof and the treatment section 9 that performs a treatment provided at a distal end of the tubular member 31. The surgeon opens or closes a finger receiver 33 provided at the operation section 32, and can thereby perform a treatment such as extirpation of a diseased tissue by opening/closing a pair of extirpation pieces making up the treatment section 9.

The tubular member 31 of the treatment instrument 4 is inserted from the insertion port 3a into the channel 3 as shown in FIG. 2. Furthermore, a sensor section 34 is provided on the rear end side of the treatment instrument 4.

This sensor section 34 is arranged, for example, at the insertion port 3a, a rotary encoder is arranged in a guide hole of the sensor section 34 and the rotary encoder contacts the outer surface of the tubular member 31 inserted in the guide hole. When the tubular member 31 moves along the guide hole, the rotary encoder rotates in contact with the guide hole and detects a position at which the distal end portion of the tubular member 31 is inserted along the longitudinal direction of the channel 3 from the amount of rotation thereof.

The position information on the distal end portion of the treatment instrument 4 at the insertion port 3a of the channel 3 detected by the sensor section 34 is inputted to a setting circuit 10a in the position determining section 10. The setting circuit 10a calculates information on the protruding position (amount of protrusion) that the distal end portion of the treatment instrument 4 protrudes from the distal end opening 3b of the channel 3 by subtracting the length of the channel 3 (acquired from the ID information) from the position information.

The present invention is not limited to the case where such a sensor section 34 is used and, for example, first and second coils that generate a magnetic field may be arranged at the distal end portion of the endoscope 2 and the distal end portion of the treatment instrument 4 respectively and a plurality of third coils that detect magnetic fields generated by the first and second coils may be arranged at predetermined positions in the periphery of a patient into whom the endoscope 2 is inserted.

It may be made possible to detect three-dimensional positions of the first and second coils arranged at the distal end portion of the endoscope 2 and the distal end portion of the treatment instrument 4 respectively and further calculate the protruding position of the distal end portion of the treatment instrument 4 that protrudes from the distal end opening 3b of the channel 3 using detection signals of the third coils.

For example, a marker 35a for facilitating optical recognition is provided at the distal end portion or in the vicinity of the distal end portion of the treatment instrument 4. As such a marker 35a, for example, two color rings in specific colors (e.g., blue and red) as shown in FIG. 1 or FIG. 2 are provided. A marker 35b may also be formed in a specific color (e.g., green) in the treatment section 9 to facilitate optical recognition.

Thus, the ring-shaped marker 35a in specific colors and the marker 35b in a specific color are provided in the vicinity of the distal end portion of the treatment instrument 4.

The position determining section 10 that receives the determination information from the processor 7 includes a threshold setting circuit 10b that sets a threshold with respect to an amount of protrusion to determine whether or not the distal end portion of the treatment instrument 4 is located (positioned) inside the image pickup region from the determination information.

The position determining section 10 then compares, through a comparison circuit 10c, the protruding position detected by the sensor section 34 via the setting circuit 10a with a threshold and outputs to the low visibility determining section 12, a determination signal as to whether or not the distal end portion of the treatment instrument 4 is positioned inside the image pickup region, that is, whether the distal end portion is inside or outside the image pickup region based on the comparison result.

The above image recognizing section 11 recognizes through image processing (or image analysis) whether or not the above markers 35a and 35b can be recognized as an image in the image signal generated by the image processing circuit 25 of the processor 7.

For this purpose, the image recognizing section 11 includes image processing means (or image analyzing means) made up of a specific color detection circuit 11a that detects a specific color (that forms the markers 35a and 35b) from the image signal and a specific shape determination circuit 11b that further determines whether or not the detected specific color portion has a specific shape (corresponding to the ring shape of the marker 35a or the shape with two lines of the marker 35b).

The image recognizing section 11 can detect specific colors of the markers 35a and 35b through the specific color detection circuit 11a and further determines the portion that can be detected as a specific color to be in a state in which the distal end portion of the treatment instrument 4 can be recognized as an image inside the image pickup region, that is, image recognizable, only when the specific shape determination circuit 11b determines the shape as a shape corresponding to the ring shape of the marker 35a and the shape with two lines of the marker 35b.

In cases of other determination results, the image recognizing section 11 determines the image of the distal end portion of the treatment instrument 4 to be unrecognizable as an image inside the image pickup region, that is, an image that cannot be recognized. The information on the recognition result by the image recognizing section 11 is outputted to the low visibility determining section 12.

Figures 3, 4:
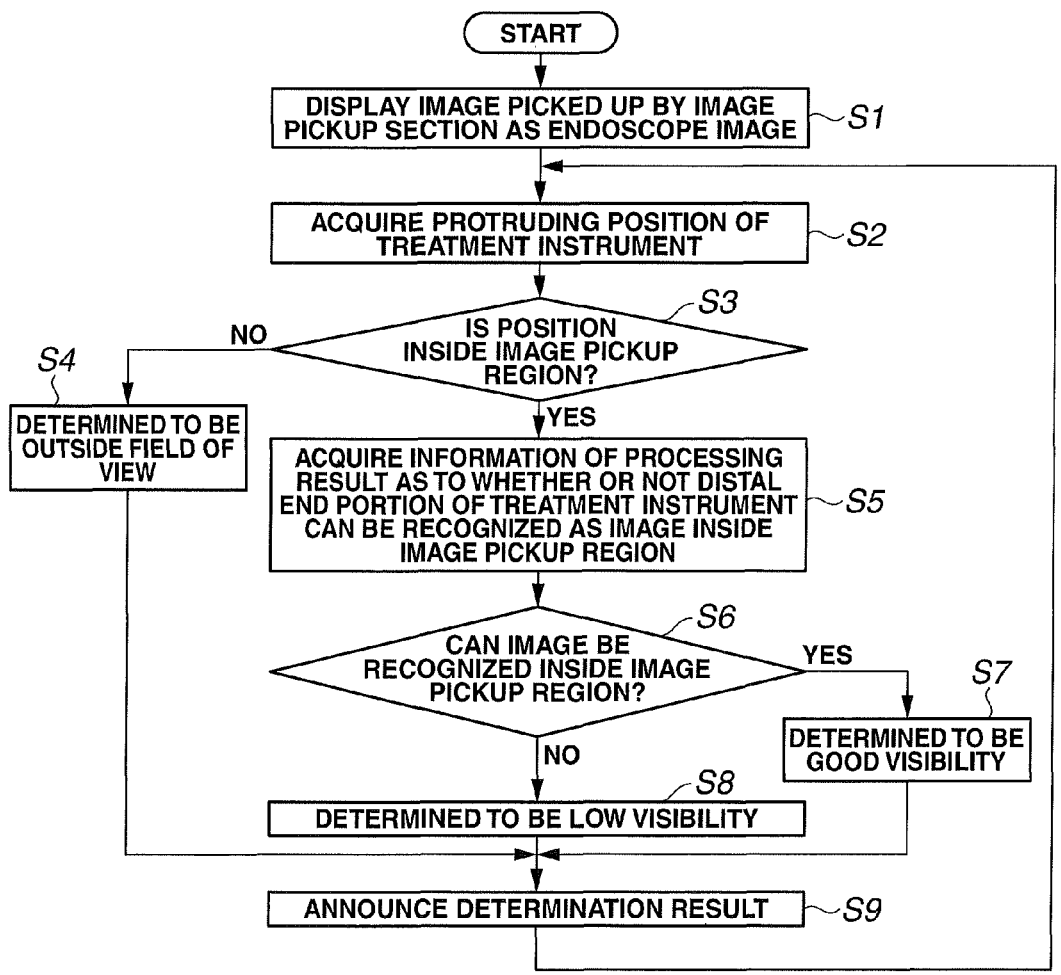
FIG. 3 is a diagram illustrating a determination result by a position determining section and a determination result of an image pickup state with respect to a treatment instrument by an image pickup section based on a recognition result by a recognizing section.
FIG. 4 is a flowchart illustrating a processing procedure for a low visibility determining method according to the first embodiment.

The low visibility determining section 12 determines the state of a picked-up image of the treatment instrument 4 picked up by the image pickup section 6 according to determination information of the position determining section 10 and the image recognizing section 11 as shown in FIG. 3. For this purpose, the low visibility determining section 12 includes an LUT 12a that receives the determination information of the position determining section 10 and the determination information of the image recognizing section 11 as, for example, address input and outputs information stored beforehand in the storage region corresponding to this address. The input/output information of the LUT 12a is as shown in the table in FIG. 3.

Furthermore, the low visibility determining section 12 outputs the information on the determination result to the image processing circuit 25 of the processor 7. The image processing circuit 25 outputs the information on the determination result superimposed on the image signal of the endoscope image to the monitor 8 and also displays the information on the determination result on the monitor 8.

Since the information on the determination result is displayed, the surgeon can immediately grasp the state thereof and when low visibility or the like occurs, the surgeon can immediately perform an operation or treatment corresponding to the state. When, for example, the state of the distal end portion of the treatment instrument 4 is changed from an observable state to an unobservable state, hidden behind a peripheral organ or the like, low visibility is announced on the same screen of the same monitor 8. Therefore, the surgeon can immediately cancel the low visibility by operating the treatment instrument 4 on the surgeon's hand side or the like.

The endoscope system 1 in such a configuration is provided with the image pickup section 6 provided at the distal end portion 17 of the insertion portion 15 of the endoscope 2 as image pickup means for performing image pickup and the position determining section 10 as determining means for determining whether or not the distal end portion of the treatment instrument 4 exists inside the image pickup region of the image pickup means as a specific observation object.

Furthermore, this endoscope system 1 is provided with the image recognizing section 11 as recognizing means for determining whether or not the specific observation object can be recognized as an image from a picked-up image inside the image pickup region picked up by the image pickup means and the low visibility determining section 12 as low visibility determination outputting means for determining, when the determining means determines that the specific observation object exists inside the image pickup region and the recognizing means cannot recognize the specific observation object as an image, that the image pickup means is in a low visibility condition and outputs a low visibility determination result.

Next, the procedure for the low visibility determining method shown in FIG. 4 including the operation in the present embodiment will be described. The surgeon inserts the insertion portion 15 of the endoscope 2 into the body cavity of a patient.

Furthermore, the treatment instrument 4 for performing a treatment on a diseased part is inserted into the channel 3. In this case, the position of the distal end portion of the treatment instrument 4 is set to the position of the distal end face of the insertion portion 15 and in this condition, the value of the protruding position of the treatment instrument 4 detected from the sensor section 34 and the setting circuit 36 is set to 0. The following description is given in a simplified manner assuming that the sensor section 34 is provided with the function of the setting circuit 10a (the sensor section 34 detects the protruding position of the distal end portion of the treatment instrument 4).

As shown in step S1 of FIG. 4, the image pickup section 6 of the endoscope 2 picks up an image of the interior of the body cavity and the picked-up image picked up by the image pickup section 6 is displayed on the monitor 8 as an endoscope image.

A picked-up image of a site to be observed such as a diseased part in the body cavity picked up by the image pickup section 6 provided at the distal end portion 17 of the insertion portion 15 is subjected to image processing by the image processing circuit 25 of the processor 7 and then displayed on a display screen of the monitor 8 as an endoscope image.

The surgeon observes the endoscope image and diagnoses the condition of the site to be observed. When a treatment is necessary, the surgeon operates the surgeon's hand side of the treatment instrument 4 and causes the distal end side of the treatment instrument 4 to protrude from the distal end face of the distal end portion 17.

The sensor section 34 detects the protruding position (from the distal end face of the endoscope 2) of the treatment instrument 4 and outputs the protruding position to the comparison circuit 10c inside the position determining section 10. That is, as shown in step S2, the position determining section 10 acquires information on the protruding position (protruding amount) of the distal end portion of the treatment instrument 4.

As shown in next step S3, the position determining section 10 compares the protruding position of the distal end portion of the treatment instrument 4 with a threshold and determines whether or not the distal end portion of the treatment instrument 4 is located inside the image pickup region.

When the determination result in step S3 shows that the protruding position of the distal end portion of the treatment instrument 4 is below the threshold, the position determining section 10 determines that the distal end portion of the treatment instrument 4 is located (exists) outside the image pickup region as shown in step S4. This determination result is outputted to the low visibility determining section 12 and the low visibility determining section 12 determines that the distal end portion of the treatment instrument 4 is located outside the field of view as shown in FIG. 3.

On the other hand, when the determination result in step S3 shows that the protruding position of the distal end portion of the treatment instrument 4 is equal to or above the threshold, the position determining section 10 determines that the distal end portion of the treatment instrument 4 is located inside the image pickup region. This determination result is outputted to the low visibility determining section 12.

When the determination result shows that the distal end portion of the treatment instrument 4 is located inside the image pickup region, the image recognizing section 11 acquires information on the processing result as to whether or not the distal end portion of the treatment instrument 4 can be recognized as an image inside the image pickup region as shown in step S5.

The present embodiment acquires information on the processing result as to whether or not the distal end portion of the treatment instrument 4 can be recognized as an image inside the image pickup region using image recognition on the markers 35a and 35b provided at the distal end portion of the treatment instrument 4.

As shown in next step S6, the image recognizing section 11 determines from the processing result of image recognition whether or not the distal end portion of the treatment instrument 4 can be recognized as an image inside the image pickup region.

When the image recognizing section 11 can recognize the image through the determination processing in step S6, it is determined that image recognition is possible as shown in FIG. 3. This determination result is outputted to the low visibility determining section 12. As shown in step S7, the low visibility determining section 12 determines that visibility is good as shown in FIG. 3. After step S7, the determination result is displayed on the monitor 8 in step S9. FIG. 2 shows this display example.

On the other hand, when the image recognizing section 11 cannot recognize the image in step S6, the image recognizing section 11 determines that image recognition is not possible as shown in FIG. 3. This determination result is outputted to the low visibility determining section 12. As shown in step S8, this low visibility determining section 12 determines that visibility is low as shown in FIG. 3.

Information on the determination results in steps S4, S7 and S8 is sent to the processor 7 and the processor 7 converts the determination result to an image signal to be displayed on the monitor 8 and then outputs the image signal to the monitor 8. As shown in step S9, the monitor 8 displays the determination result, announcing the determination result to the surgeon. The processing in step S9 is not limited to the case where the determination result is announced by a display, but the determination result may also be announced with a voice. Alternatively, it may be also possible to adopt processing (low visibility output processing) of outputting the determination result to announcing means (by a display or voice).

By receiving announcement of low visibility, the surgeon can immediately perform a treatment corresponding to the low visibility.

By checking the state of the treatment instrument 4 on the distal end side from the endoscope image, the surgeon can more easily and immediately grasp the cause of low visibility such as the distal end side of the treatment instrument 4 being hidden behind an organ peripheral to the site to be treated.

After the processing in step S9, the process returns to the processing in step S2 and the processing in steps S2 to S9 is repeated.

The low visibility determining method formed in the first embodiment in aforementioned FIG. 4 includes step S1 as a display step of displaying a picked-up image which is an image of a site to be observed in the body cavity picked up by the image pickup section as an endoscope image and step S2 as a treatment instrument position acquiring step of acquiring the position of the distal end portion of the treatment instrument that performs a treatment on the site to be observed.

Furthermore, the low visibility determining method includes step S3 as a position determining step of determining whether or not the position of the distal end portion of the treatment instrument is located inside the image pickup region as a region of the picked-up image and step S5 as a recognizing step of performing image recognition as to whether or not the distal end portion of the treatment instrument can be recognized as an image inside the image pickup region through image processing on the picked-up image.

Furthermore, the low visibility determining method also includes determining (step S8) in the position determining step that the distal end portion of the treatment instrument is located inside the image pickup region, determining, when the recognition result in the recognizing step shows that the distal end portion of the treatment instrument cannot be recognized as an image inside the image pickup region, that visibility is low and step S9 as a low visibility determination outputting step of outputting the low visibility determination result.

According to the present embodiment operating in this way, in a state in which the image pickup means picks up an image, it is possible to immediately determine that although the distal end side of the treatment instrument as a specific observation object is located inside the image pickup region, a low visibility state is present in which the distal end side of the treatment instrument cannot be observed.

Furthermore, when a low visibility state in which observation is not possible is present, means for announcing it to the surgeon is provided, and the surgeon can thereby immediately recognize the low visibility state. The surgeon can then immediately and more easily take an appropriate measure even when a low visibility state is generated.

A case with the treatment instrument 4 that manually extirpates a lesioned tissue or the like has been described in the present embodiment, but the present invention is also applicable to a case with a treatment instrument having a different function. Furthermore, the present invention is also applicable to a high-frequency treatment instrument that performs a treatment using high-frequency electric energy or an energy treatment instrument such as an ultrasound treatment instrument that performs a treatment using ultrasound energy.

Second Embodiment

Figure 5:
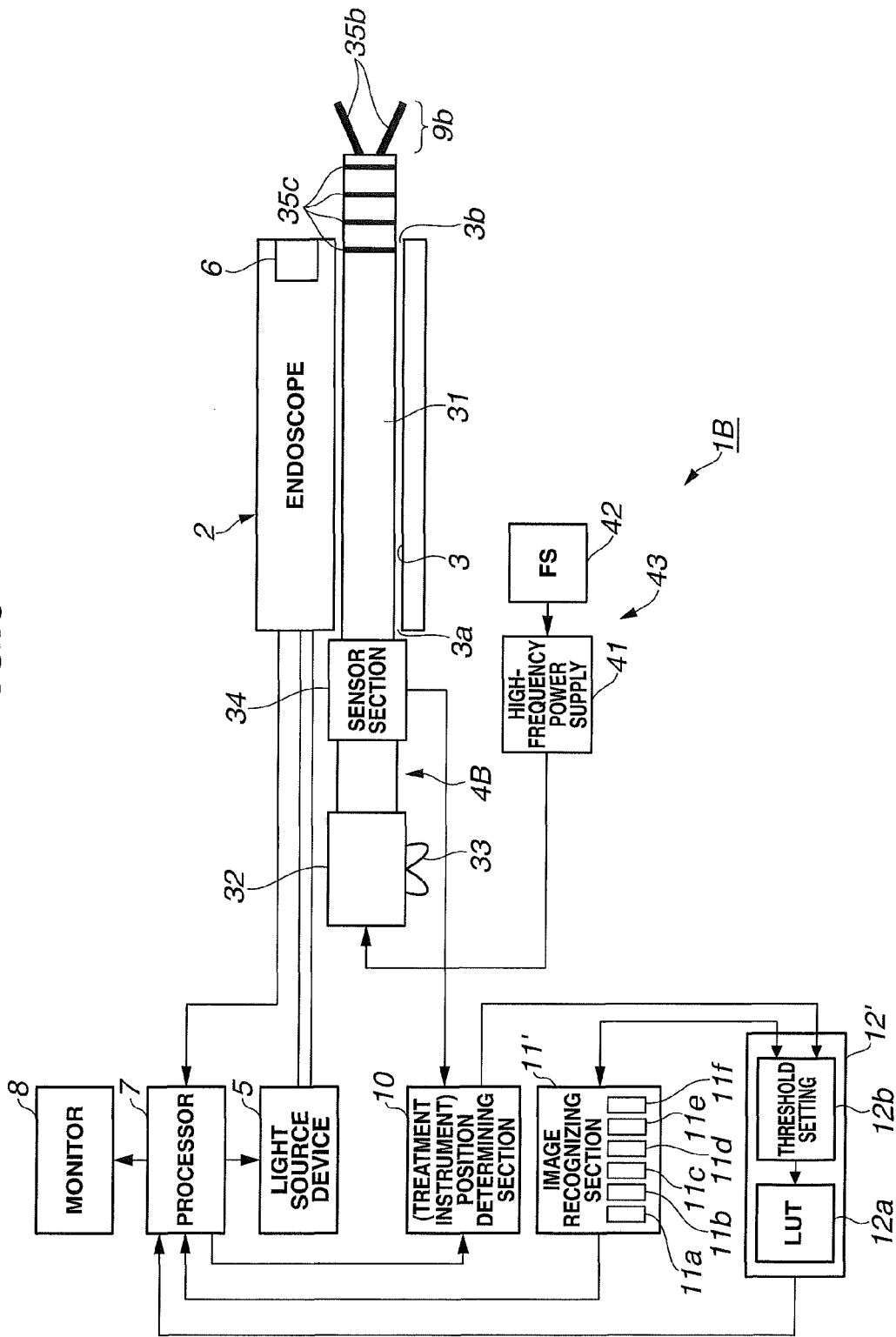
FIG. 5 is a configuration diagram illustrating an overall configuration of an endoscope system according to a second embodiment of the present invention.
Figure 6:
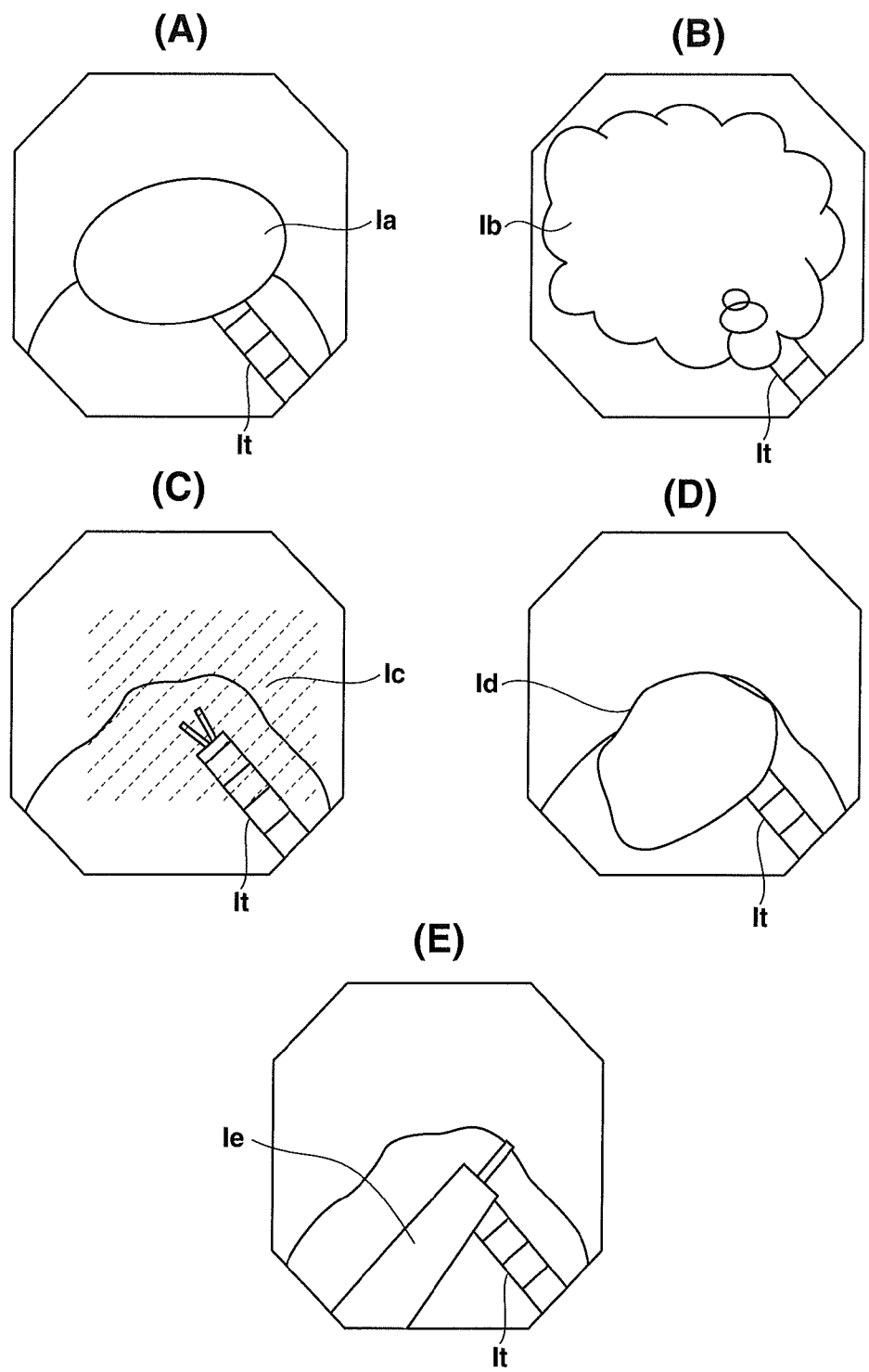
FIG. 6(A) to FIG. 6(E) are diagrams schematically illustrating examples of endoscope images when the type of an obstacle that causes low visibility is internal organ, smoke, mist, hemorrhage and other treatment instrument.

Next, a second embodiment of the present invention will be described with reference to FIG. 5 to FIG. 9. FIG. 5 illustrates an overall configuration of an endoscope system 1B according to the second embodiment of the present invention.

The endoscope system 1B shown in FIG. 5 corresponds to the endoscope system 1 in FIG. 1 using a high-frequency treatment instrument 4B that performs a treatment using high-frequency electric energy instead of the treatment instrument 4 and this high-frequency treatment instrument 4B is connected to a high-frequency power supply apparatus 41 as an electric energy supply apparatus.

Furthermore, this high-frequency power supply apparatus 41 is connected to a foot switch (abbreviated as "FS" in FIG. 5) 42 that performs an instruction operation to output or stop outputting a high-frequency current (ON/OFF). The high-frequency treatment instrument 4B, the high-frequency power supply apparatus 41 and the foot switch 42 constitute a high-frequency electrocoagulation apparatus 43.

This high-frequency treatment instrument 4B includes, for example, a treatment section 9b made up of a pair of knives (simply abbreviated as "knives") that opens/closes for extirpation at a distal end portion of a tubular member 31 as in the case of the first embodiment.

When the foot switch 42 is switched ON, a high-frequency current is supplied to the knives making it possible through a high-frequency current to extirpate a living tissue contacting the knives, which is an object to be treated.

Furthermore, when the image recognizing section 11 and the low visibility determining section 12 in FIG. 2 determine low visibility, an image recognizing section 11' and a low visibility determining section 12' in the present embodiment are provided with a function of further estimating an obstacle or a type of obstacle responsible for low visibility and announce the estimation result to the surgeon.

For this purpose, the image recognizing section 11' includes, for example, a histogram calculation circuit 11c that calculates a histogram as a distribution of the number of pixels of brightness values of image signals of three primary colors of R, G and B. Furthermore, the image recognizing section 11' includes a smoke detecting circuit 11d and a mist detection circuit 11e that detect smoke candidates and mist candidates respectively.

Furthermore, the image recognizing section 11' includes another treatment instrument detection circuit 11f that detects another treatment instrument to also estimate a case where the other treatment instrument used together with the high-frequency treatment instrument 4B constitutes an obstacle that causes low visibility of the distal end side of the high-frequency treatment instrument 4B.

Furthermore, a ring-shaped marker 35c having more rings than in the first embodiment and a line-shaped marker 35b are provided in the vicinity of the distal end portion of the high-frequency treatment instrument 4B in the present embodiment. That is, the ring-shaped marker 35c formed to be longer in the longitudinal direction thereof than in the case of the first embodiment and set to have a specific color so as to cover a predetermined length is provided in the vicinity of the distal end portion of the high-frequency treatment instrument 4B.

Therefore, the present embodiment also uses the specific color detection circuit 11a and the specific shape determination circuit 11b described in the first embodiment.

However, the specific color detection circuit 11a of the present embodiment has a function of detecting, for example, three or more specific colors and is designed to be able to determine whether all (or substantially all) the distal end portion side of the high-frequency treatment instrument 4B can be detected as an image or part of the distal end portion side of the high-frequency treatment instrument 4B can be detected as an image according to the number of rings when the marker 35c as well as the marker 35b can be detected.

Furthermore, signals detected by the specific color detection circuit 11a to the other treatment instrument detection circuit 11f are inputted to the low visibility determining section 12' and upon determining the low visibility from these signals, the low visibility determining section 12' further estimates an obstacle or a type of obstacle that causes the low visibility.

For this purpose, the low visibility determining section 12' includes a threshold setting section 12b that stores a threshold for estimating an obstacle or a type thereof from a histogram of the number of R, G and B pixels calculated by the histogram calculation circuit 11c, the smoke detecting circuit 11d and the mist detection circuit 11e.

The low visibility determining section 12' inputs the comparison output obtained from a comparison with a threshold of the threshold setting section 12b to, for example, a lookup table (LUT) 12a, thereby estimates an obstacle or a type thereof and outputs the estimated determination result.

For example, FIG. 6(A) to FIG. 6(E) show examples of endoscope images when an organ, smoke, mist, hemorrhage or other treatment instrument (as an obstacle) causes low visibility on the distal end portion side of the high-frequency treatment instrument 4B. That is, images of the organ, smoke, mist, hemorrhage and other treatment instrument which constitute obstacles in the endoscope image in FIG. 6(A) to FIG. 6(E) are represented by Ia, Ib, Ic, Id and Ie, respectively. Furthermore, the image (of the distal end portion side) of the high-frequency treatment instrument 4B is represented by It.

Figure 7A:
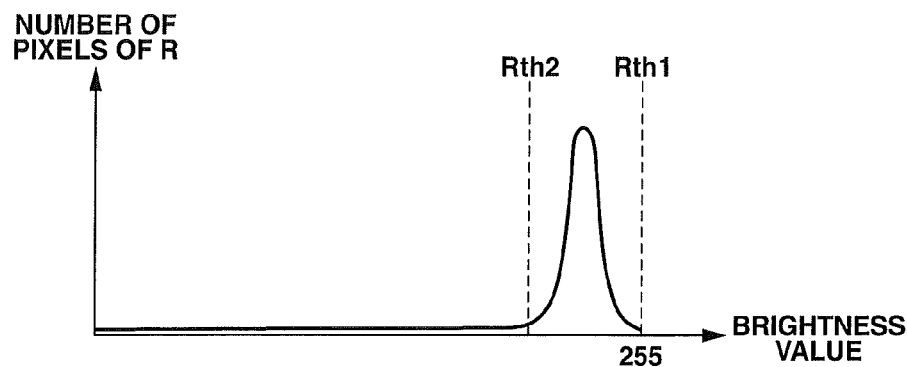
FIG. 7A is a diagram illustrating a characteristic example of a histogram of a distribution of the number of pixels with brightness values of image signals of R and G corresponding to a case where the obstacle is an internal organ.
Figure 7B:
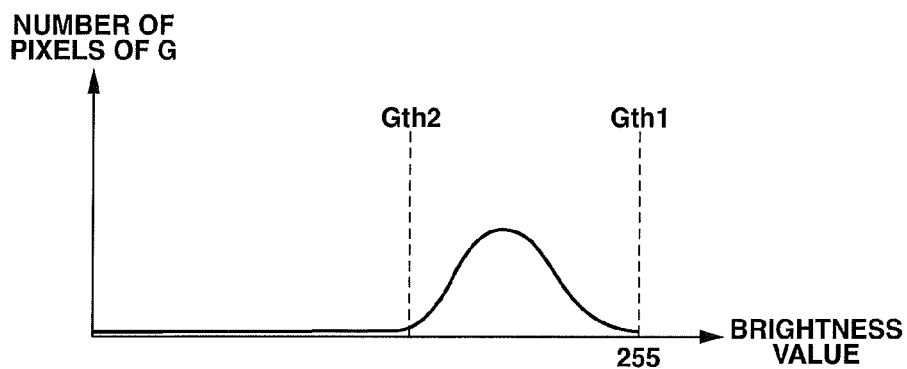
FIG. 7B is a diagram illustrating an estimation table using thresholds to estimate the case where the obstacle is an internal organ in correspondence to FIG. 7A.

Furthermore, FIG. 7A shows a histogram example when the organ in FIG. 6(A) constitutes an obstacle and a setting example of thresholds set to estimate that the obstacle is the organ.

The upper diagram in FIG. 7A shows a setting example of thresholds Rth1 and Rth2 set for a histogram of brightness values of an image signal of R and the lower diagram shows a setting example of thresholds Gth1 and Gth2 set for a histogram of an image signal of G. The brightness value on the horizontal axis is shown in a case of 8 bits, for example.

Although a histogram of brightness values regarding the image signal of B is not shown, thresholds Bth1 and Bth2 are set in substantially the same way as in the case of the histogram for the image signal of G. When low visibility occurs, the thresholds shown in FIG. 7A are used and the low visibility determining section 12' estimates that the obstacle is an organ using the LUT 12a only when a predetermined condition shown in FIG. 7B (condition indicated by ○ in FIG. 7B) is satisfied.

That is, the low visibility determining section 12' estimates that the obstacle is an organ when the condition that the number of pixels R of the image signal of R (represented by "R" for simplicity) is Rth1>R>Rth2, the condition that the number of pixels G of the image signal of G (represented by "G" for simplicity) is Gth1>G>Gth2 and the condition that the number of pixels B of the image signal of B (represented by "B" for simplicity) is Bth1>B>Bth2.

A case where such conditions are satisfied is described as a case that corresponds to an organ estimation table. When such a condition is not satisfied, that is, a case that does not corresponds to the organ estimation table, the obstacle is estimated not to be attributable to the organ.

Furthermore, when, for example, the condition of Rth1>R>Rth2, the condition of Gth2>G and the condition of Bth2>B are satisfied, the visibility determining section 12' estimates that the obstacle is a hemorrhage. A case that such a condition is satisfied is described as a case that corresponds to a hemorrhage estimation table.

When such a condition is not satisfied, the obstacle is estimated not to be attributable to a hemorrhage.

Furthermore, the smoke detecting circuit 11d detects white smoke as shown in FIG. 6(B) from the image signal. For example, this smoke detecting circuit 11d detects whether or not R, G and B image signals having substantially the same brightness value exceeding a predetermined value exist two-dimensionally using a window type comparator.

The smoke detecting circuit 11d then outputs the signal of the detection result to the low visibility determining section 12'. When the regions in which the smoke detecting circuit 11d detects R, G and B image signals having substantially the same brightness value exceeding a predetermined threshold exist consecutively, the low visibility determining section 12' estimates, using the LUT 12a, that the obstacle is smoke considering it to correspond to the smoke estimation table. In other cases, the obstacle is estimated not to be smoke.

Furthermore, the mist detection circuit 11e detects whether or not R, G and B image signals having substantially the same brightness value exceeding a predetermined value exist two-dimensionally using a window type comparator as in the case of the smoke detecting circuit 11d.

However, the mist detection circuit 11e detects whether or not R, G and B image signals having substantially the same brightness value exceeding a predetermined value exist not consecutively but discretely. The mist detection circuit 11e may also be configured to simply detect in any one of R, G and B image signals whether or not many brightness values exceeding a predetermined value are detected discretely over a two-dimensional region.

As shown in FIG. 6(C), mist has a brightness value exceeding a predetermined value and is generated as fog or rain, and it is thereby possible to accurately estimate a case where the type of an obstacle is mist by detecting a feature thereof (feature that many such brightness values are generated discretely in a two-dimensional region).

The detection result of this mist detection circuit 11e is outputted to the low visibility determining section 12'. When the obstacle corresponds to the feature of mist, that is, the determination result corresponds to the mist estimation table, the low visibility determining section 12' determines using the LUT 12a, that the obstacle is mist. When the determination result does not correspond to this mist estimation table, the low visibility determining section 12' estimates that the obstacle is not mist.

Furthermore, the other treatment instrument detection circuit 11f detects whether or not the obstacle is the other treatment instrument with reference to preset features of the treatment instrument such as the shape, color of the distal end side. When, for example, a brightness value exceeding a threshold and a tubular or arm shape are detected from the image signal, the other treatment instrument detection circuit 11f detects that the obstacle is the other treatment instrument. This detection result is outputted to the low visibility determining section 12'.

When the low visibility determining section 12' determines that the obstacle corresponds to none of the aforementioned organ, smoke, mist or hemorrhage, and the other treatment instrument detection circuit 11f detects that the obstacle is the other treatment instrument, the low visibility determining section 12' determines that the obstacle is the other treatment instrument according to the other treatment instrument estimation table using the LUT 12a.

Furthermore, when the obstacle corresponds to none of the aforementioned organ, smoke, mist, hemorrhage or other treatment instrument, the low visibility determining section 12' determines or estimates that another obstacle is the cause. The rest of the configuration is similar to that of the first embodiment.

The low visibility determining method according to the second embodiment having such a configuration shown in FIG. 8 will be described.

Figure 8:
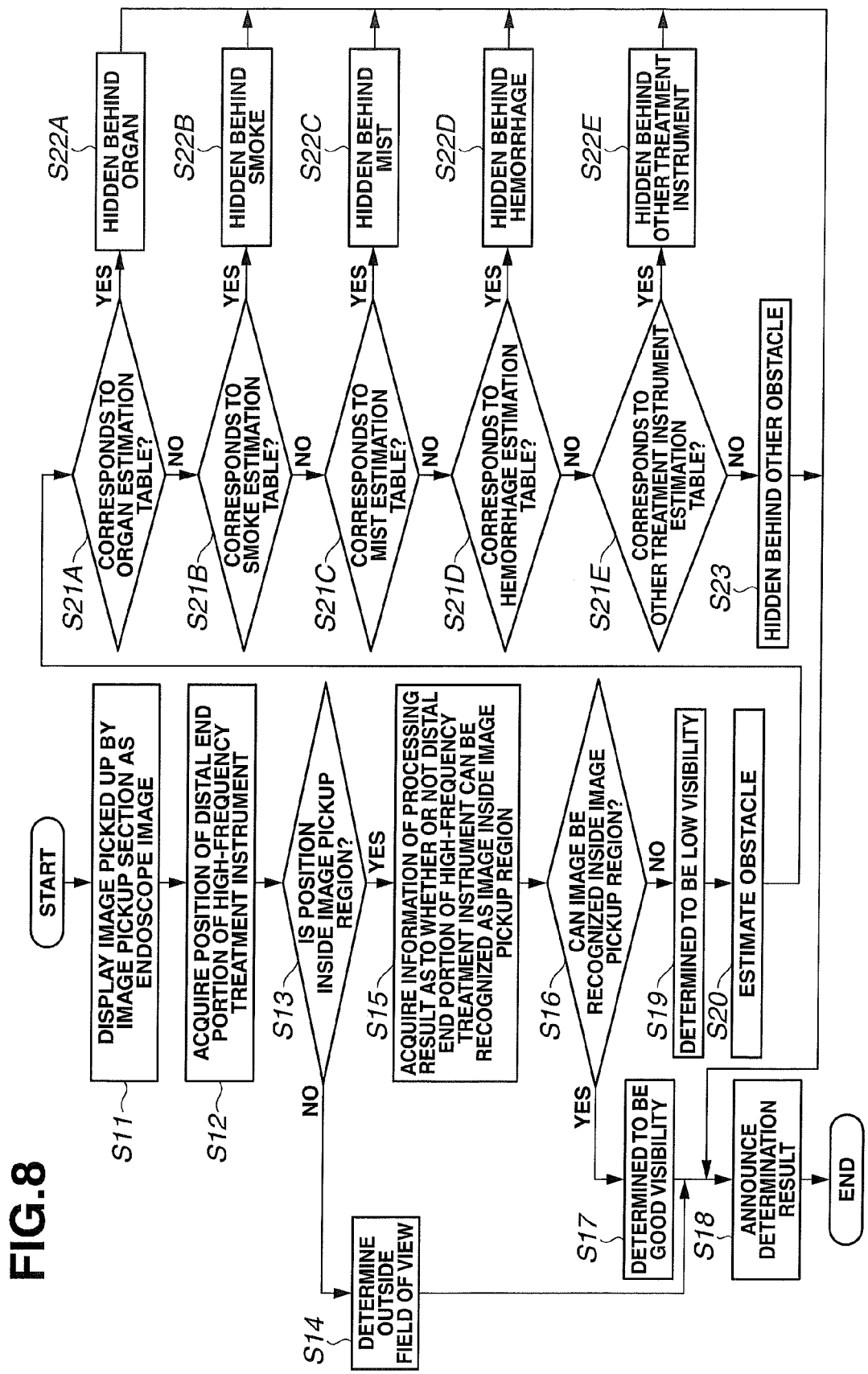
FIG. 8 is a flowchart illustrating a processing procedure for a low visibility determining method according to the second embodiment of the present invention.

Initial steps S11 to S18 in FIG. 8 are processes substantially the same as those in steps S1 to S8 in FIG. 4.

In initial step S11, the image pickup section 6 picks up an image of a site to be observed such as a diseased part in the body cavity and displays the picked-up image on the monitor 8 as an endoscope image.

In next step S12, the sensor section 34 acquires the position of the distal end portion of the high-frequency treatment instrument 4B that performs a treatment on the site to be observed. In next step S13, the position determining section 10 determines whether or not the position of the distal end portion of the high-frequency treatment instrument 4B is located inside the image pickup region.

Upon determining that the distal end portion of the high-frequency treatment instrument 4B is not located inside the image pickup region, the position determining section 10 determines that the distal end portion of the high-frequency treatment instrument 4B is located (exists) outside the image pickup region as shown in step S14.

This determination result is outputted to the low visibility determining section 12' and the low visibility determining section 12' determines that the distal end portion of the high-frequency treatment instrument 4B is located outside the field of view.

On the other hand, the determination result indicating that the distal end portion of the high-frequency treatment instrument 4B is located inside the image pickup region is outputted to the low visibility determining section 12.

In the case of the determination result indicating that the distal end portion of the high-frequency treatment instrument 4B is located inside the image pickup region, the image recognizing section 11' acquires information on the processing result as to whether or not the distal end portion of the high-frequency treatment instrument 4B can be recognized as an image inside the image pickup region as shown in step S15.

As shown in next step S16, the image recognizing section 11' determines from the processing result of the image recognition whether or not the distal end portion of the high-frequency treatment instrument 4B can be image-recognized inside the image pickup region.

When the recognizing section 11' can image-recognize the distal end portion in step S16, it is determined that image recognition is possible as shown in FIG. 3. This determination result is outputted to the low visibility determining section 12.

As shown in next step S17, the low visibility determining section 12 determines that visibility is good as shown in FIG. 3. The determination result is displayed on the monitor 8 in step S18 after step S17. The determination result is then announced to the surgeon.

On the other hand, when the image recognizing section 11 cannot image-recognize the distal end portion in step S16, it is determined that image recognition is not possible as shown in FIG. 3. This determination result is outputted to the low visibility determining section 12. As shown in step S19, the low visibility determining section 12 then determines that visibility is low as shown in FIG. 3.

In the present embodiment, when low visibility is determined, the determination result is sent to the image recognizing section 11'. In next step S20, the image recognizing section 11' performs image processing of estimating an obstacle (or the type thereof) responsible for the low visibility. In next step S20, the image recognizing section 11' outputs information on the image processing such as a histogram calculated by the histogram calculation circuit 11c to the low visibility determining section 12'.

In next step S21A, the low visibility determining section 12' determines whether or not the inputted information corresponds to a condition (organ estimation table) when the obstacle is an organ. When the determination result shows that the inputted information corresponds to a condition when the obstacle is an organ, the low visibility determining section 12' determines in next step S22A that the distal end portion of the high-frequency treatment instrument 4B is hidden behind the organ.

The low visibility determining section 12' then sends the information on the determination result to the processor 7 and the processor 7 outputs the information on the determination result that there is a high possibility that the distal end portion of the high-frequency treatment instrument 4B may be hidden behind the organ to the monitor 8. In step S18, the monitor 8 displays the determination result indicating that there is a high possibility that the distal end portion of the high-frequency treatment instrument 4B may be hidden behind the organ and announces the determination result to the surgeon.

When the inputted information does not correspond to the organ estimation table in step S21A, the low visibility determining section 12' determines in step S21B whether or not the inputted information corresponds to a condition when the obstacle is smoke (smoke estimation table). When the determination result shows that the inputted information corresponds to a condition when the obstacle is smoke, the low visibility determining section 12' determines in next step S22B that the distal end portion of the high-frequency treatment instrument 4B is hidden behind smoke.

The low visibility determining section 12' sends the information on the determination result to the processor 7 and the processor 7 outputs the information on the determination result that there is a high possibility that the distal end portion of the high-frequency treatment instrument 4B may be hidden behind smoke to the monitor 8. In step S18, the monitor 8 displays the determination result indicating that there is a high possibility that the distal end portion of the high-frequency treatment instrument 4B may be hidden behind smoke and announces the determination result to the surgeon.

When the inputted information does not correspond to the smoke estimation table in step S21B, the low visibility determining section 12' determines in step S21C whether or not the inputted information corresponds to the condition when the obstacle is mist (mist estimation table).

When the determination result shows that the inputted information corresponds to the mist estimation table, the low visibility determining section 12' determines in next step S22C that the distal end portion of the high-frequency treatment instrument 4B is hidden behind the mist.

The low visibility determining section 12' then sends the information on the determination result to the processor 7 and the processor 7 outputs the information on the determination result that there is a high possibility that the distal end portion of the high-frequency treatment instrument 4B may be hidden behind mist to the monitor 8. In step S18, the monitor 8 displays a determination result indicating that there is a high possibility that the distal end portion of the high-frequency treatment instrument 4B may be hidden behind mist and announces the determination result to the surgeon.

In step S21C, when the inputted information does not correspond to the mist estimation table, the low visibility determining section 12' determines in step S21D whether or not the inputted information corresponds to a condition when the obstacle is a hemorrhage (hemorrhage estimation table). When the inputted information corresponds to this, the low visibility determining section 12' determines in step S22D that the distal end portion of the high-frequency treatment instrument 4B is hidden behind a hemorrhage (portion).

Furthermore, in step S18, the monitor 8 displays a determination result indicating that there is a high possibility that the distal end portion of the high-frequency treatment instrument 4B may be hidden behind a hemorrhage portion and announces the determination result to the surgeon.

In step S21D, when the inputted information does not correspond to the hemorrhage estimation table, the low visibility determining section 12' determines in step S21E whether or not the inputted information corresponds to a condition (other treatment instrument estimation table) when the obstacle is another treatment instrument.

When the inputted information corresponds to this case, the low visibility determining section 12' determines in step S22E that the distal end portion of the high-frequency treatment instrument 4B is hidden behind the other treatment instrument. Furthermore, in step S18, the monitor 8 displays a determination result indicating that there is a high possibility that the distal end portion of the high-frequency treatment instrument 4B may be hidden behind the other treatment instrument and announces the determination result to the surgeon.

When the inputted information does not correspond to the other treatment instrument estimation table, the low visibility determining section 12' determines in step S21E that the inputted information corresponds to an obstacle other than the aforementioned organ, smoke, mist, hemorrhage or other processing instrument (called "other obstacle").

The low visibility determining section 12' determines in step S23 that the distal end portion of the high-frequency treatment instrument 4B is hidden behind the other obstacle. Furthermore, in step S18, the monitor 8 displays a determination result indicating that there is a high possibility that the distal end portion of the high-frequency treatment instrument 4B may be hidden behind the other obstacle and announces the determination result to the surgeon.

According to the present embodiment, when visibility is low, the monitor 8 displays an obstacle or the type thereof responsible for the low visibility, and therefore the surgeon can immediately perform a treatment corresponding to the type of the obstacle. In addition, the present embodiment has effects similar to those of the first embodiment.

Figure 9:
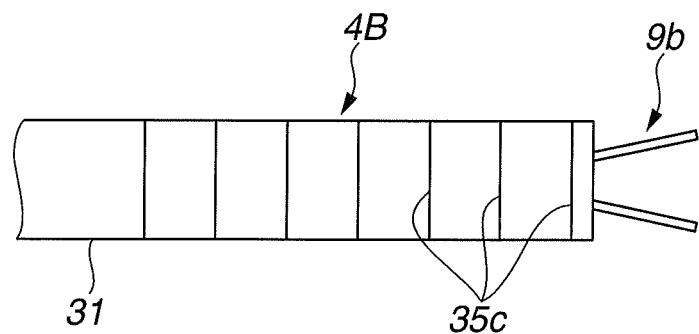
FIG. 9 is a diagram illustrating a distal end side portion of a treatment instrument according to a modification example.

In the second embodiment, the ring-shaped marker 35c is provided in the vicinity of the distal end portion of the high-frequency treatment instrument 4B in the longitudinal direction thereof, but as shown in FIG. 9, a scale 35d may be provided in the longitudinal direction in the vicinity of the distal end portion.

From the scale portion recognized when this scale 35d is image-recognized, it is possible to determine the recognized condition of the distal end side portion of the high-frequency treatment instrument 4B (whether the whole or part of the distal end side portion can be recognized or the like). In this case, a circuit that detects the scale portion is used instead of the specific color detection circuit 11a. Furthermore, the thickness of the scale or the like may be regularly changed to facilitate identification of each scale portion.

The aforementioned marker 35b may be formed in the treatment section 9b, but in addition, the treatment section 9b may also be coated with a member of a high reflection factor to facilitate image recognition in a brighter condition.

A case with the high-frequency treatment instrument 4B has been described in the present embodiment which performs a treatment using high-frequency electric energy, but the present invention is likewise applicable to an ultrasound treatment instrument that performs a treatment using ultrasound energy.

Third Embodiment

Figure 10:
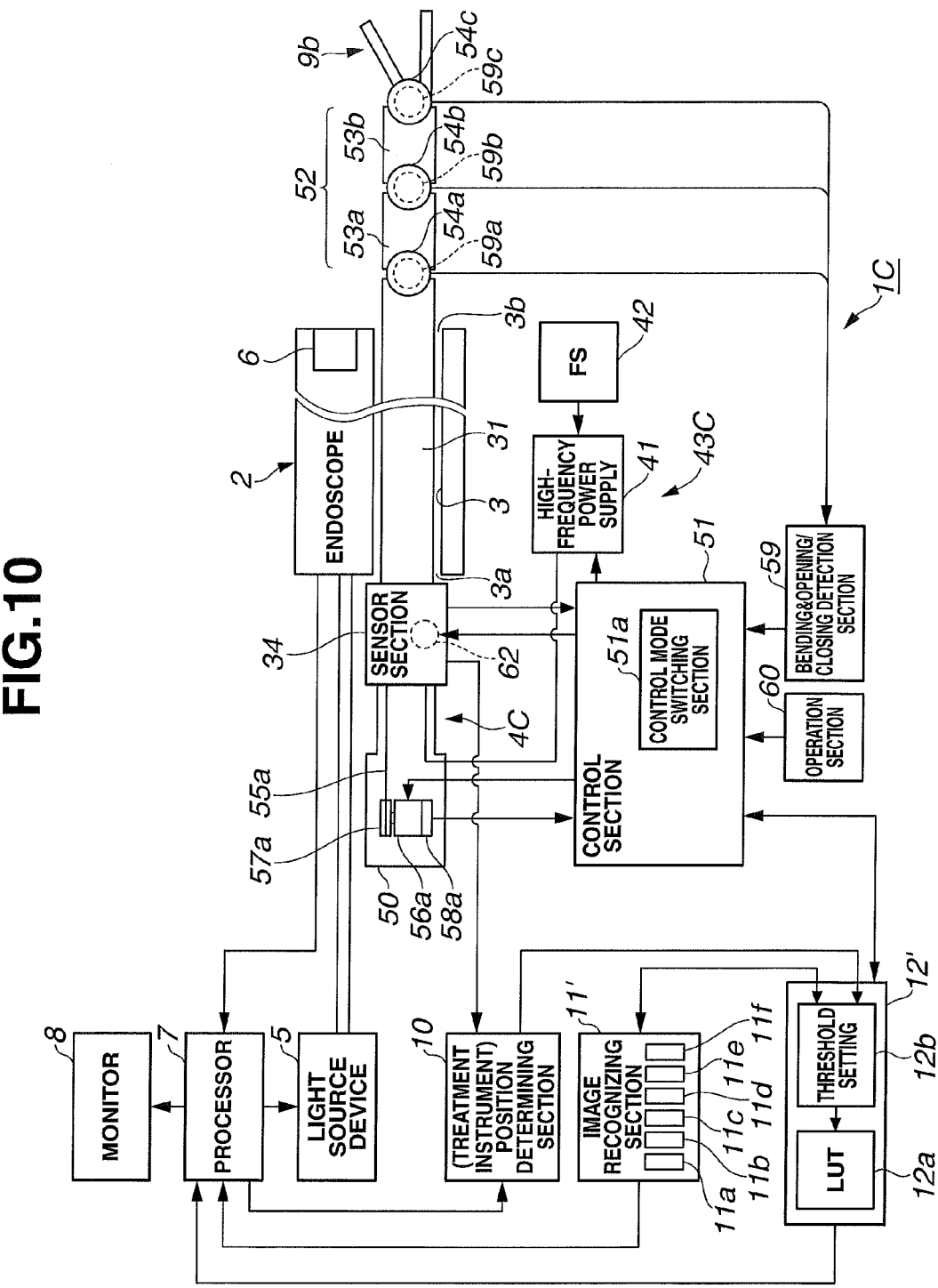
FIG. 10 is a configuration diagram illustrating an overall configuration of an endoscope system according to a third embodiment of the present invention.

Next, a third embodiment of the present invention will be described with reference to FIG. 10 to FIG. 12. FIG. 10 is a diagram illustrating an overall configuration of an endoscope system 1C according to the third embodiment of the present invention.

The endoscope system 1C corresponds to the endoscope system 1B according to the second embodiment shown in FIG. 5 using an active high-frequency treatment instrument (simply abbreviated as "high-frequency treatment instrument") 4C provided with a drive section 50 that actively drives a moving section instead of the manual high-frequency treatment instrument 4B. This high-frequency treatment instrument 4C, a high-frequency power supply apparatus 41 and a foot switch 42 form a high-frequency electrocoagulation apparatus 43C.

Furthermore, the endoscope system 1C of the present embodiment is provided with a control section 51 that controls operation of the high-frequency treatment instrument 4C and also controls an energy supply operation for the high-frequency power supply apparatus 41 as an energy supply apparatus. This control section 51 controls operation of the high-frequency electrocoagulation apparatus 43C according to a determination result by a low visibility determining section 12'.

The high-frequency treatment instrument 4C is provided with a plurality of joints 53a and 53b making up a bending portion 52 on the distal end side of a tubular member 31. Joint shafts 54a, 54b and 54c making up a pivotable moving section are provided at a distal end of the tubular member 31 and a rear end of the joint 53a, at a distal end of the joint 53a and a rear end of the joint 53b, and at a distal end of the joint 53b, respectively.

While the joint shafts 54a and 54b make up the bending portion 52, the joint shaft 54c makes up an opening/closing mechanism for opening/closing a pair of knives making up a treatment section 9b, for example, by rotating one of the pair of knives.

Distal ends of pairs of wires 55a, 55b and 55c are fixed to the joint shafts 54a, 54b and 54c so as to wind around the shafts, respectively and rear ends of the pairs of wires 55a, 55b and 55c are fixed, for example, to pulleys 57a, 57b and 57c attached to the axes of rotation of motors 56a, 56b and 56c mounted in the drive section 50 provided at the rear end of the tubular member 31.

FIG. 10 only shows the wire 55a, motor 56a and pulley 57a in a simplified form.

Each motor 56i (i=a, b, c) making up drive means is driven to rotate by a motor drive signal supplied from the control section 51. An encoder 58i (only 58a is shown in FIG. 10) is attached to the axis of rotation of each motor 56i and the encoder 58i detects the angle of rotation of the motor 56i and outputs the angle of rotation to the control section 51.

Furthermore, the joint shafts 54a, 54b and 54c are provided with sensors 59a, 59b and 59c that detect the respective angles of rotation. The detection signal detected by each sensor 59i is inputted to a bending & opening/closing detection section 59. This bending & opening/closing detection section 59 detects (bending information made up of) the bending direction and bending angle of the bending portion 52 from the detection signals of the sensors 59a and 59b, and also detects the opening/closing angle of the knives from the detection signal of the sensor 59c.

The bending information on the bending portion 52 detected by the bending & opening/closing detection section 59 and the opening/closing information of the knives are inputted to the control section 51.

Furthermore, an operation section 60 such as a joystick that performs operation of instructing the bending portion 52 to bend and instructing the knives to open/close is connected to the control section 51. The control section 51 performs control operation of driving the drive section 50 according to an instruction operation from the operation section 60. This control section 51 is connected not only to the low visibility determining section 12' but also to the high-frequency power supply apparatus 41.

The control section 51 includes a normal control mode (first control mode) for performing control operation corresponding to the operations by the foot switch 42 and the operation section 60 and a second control mode for performing control operation corresponding to the low visibility determination result by the low visibility determining section 12' (to be more specific, the determination result of the type of an obstacle).

In other words, when the low visibility determination result is not inputted from the low visibility determining section 12', the control section 51 performs control operation in the normal control mode. The control section 51 has a function of a control mode switching section 51a that switches the control mode so as to perform control operation by switching from the normal control mode to a second control mode when the low visibility determination result is inputted from the low visibility determining section 12'.

In FIG. 10, the joints 53a and 53b have been described as being pivotable around the joint shafts 54a and 54b, respectively, but the bending portion 52 may also have a structure of being pivotable in a direction orthogonal to the joint shafts 54a and 54b. Furthermore, FIG. 10 shows the two joints 53a and 53b, but the bending portion 52 may also be configured with more joints.

Figure 11:
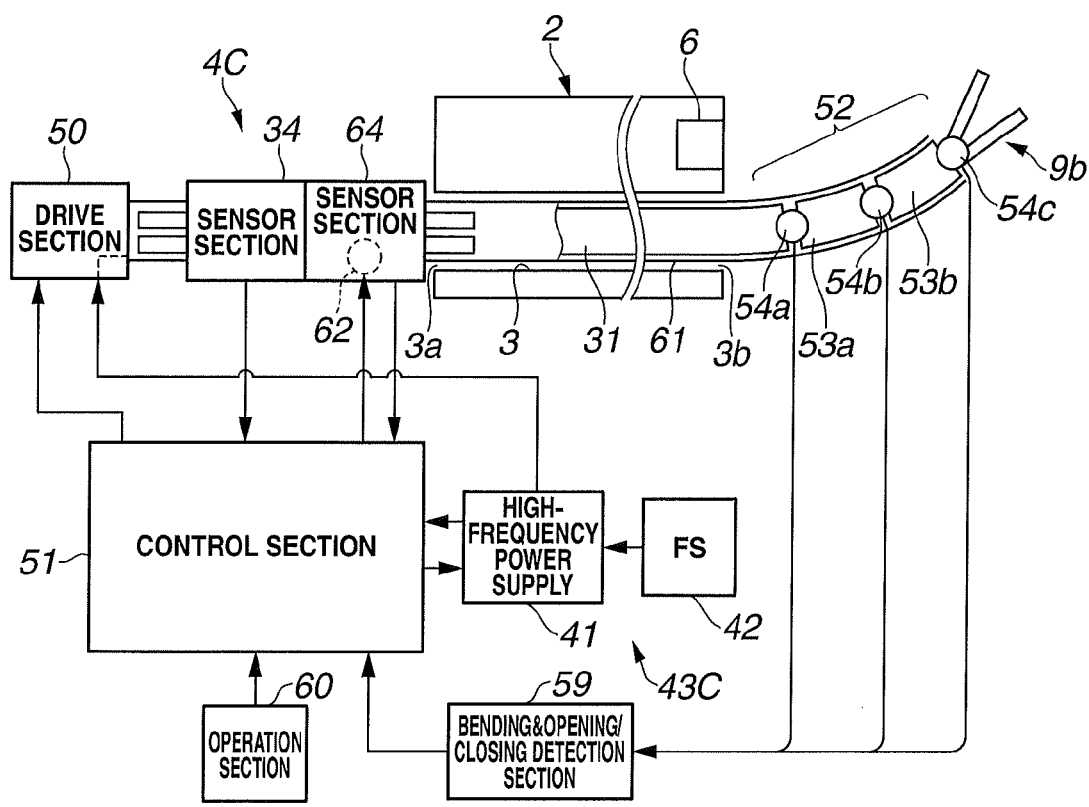
FIG. 11 is a diagram illustrating a configuration example of a treatment instrument provided with an external tube.

Furthermore, according to the present embodiment, the tubular member 31 is moved in the longitudinal direction of a channel 3 under the control of the control section 51 so that the treatment section 9b formed of knives in particular may be accommodated inside the channel 3 or accommodated inside an external tube 61 shown in FIG. 11.

In the configuration in FIG. 10, for example, a sensor section 34 includes a motor 62 (that moves the high-frequency treatment instrument 4C and constitutes moving means for retracting the treatment section 9b) whose axis of rotation is connected to a roller in addition to the rotary encoder described in the aforementioned first embodiment.

The moving operation of the motor 62 is controlled by the control section 51. Driving this motor 62 to rotate makes it possible to move the tubular member 31 which moves in sliding contact with the roller in the longitudinal direction thereof to accommodate the knives that form the treatment section 9b at the distal end portion of the high-frequency treatment instrument 4C inside the channel 3 (that is, retract the knives into a state in which the knives do not protrude from a distal end opening 3b of the channel 3).

Although FIG. 10 shows the configuration in which the bending portion 52 is formed at the distal end portion of the tubular member 31, it is also possible to adopt a configuration provided with a flexible external tube 61 that accommodates the tubular member 31 and the bending portion 52 on the distal end side thereof as shown in FIG. 11.

In this case, in the case of the external tube 61, a sensor section 64 arranged at the position of an insertion port 3a of the channel 3 detects a predetermined position of the external tube 61, for example, the position of the distal end opening of the external tube 61 from the position of the insertion port 3a.

Furthermore, a predetermined position of the tubular member 31 inside the external tube 61, for example, the position of the distal end portion is detected by the sensor section 34 arranged adjacent to the sensor section 63. A roller and a rotary encoder (not shown) in this sensor section 34 have sliding contact with the tubular member 31 inside the external tube 61 via long grooves formed in a plurality of locations in the circumferential direction on the rear end side of the external tube 61.

Furthermore, in addition to the aforementioned rotary encoder, a motor 62 whose axis of rotation is connected to the roller is arranged inside the sensor section 63.

Driving this motor 62 to rotate makes it possible to move the tubular member 31 which moves in sliding contact with the roller in the longitudinal direction thereof to accommodate the knives at the distal end portion of the high-frequency treatment instrument 4C inside the distal end opening of the external tube 61 (that is, retract the knives into a state in which the knives do not protrude from the distal end opening). Detection signals of the sensor sections 34 and 63 are inputted to the control section 51 and when the control section 51 receives a low visibility determination result from the low visibility determining section 12', the control section 51 controls the operation of the motor 62. The rest of the configuration is similar to that of the second embodiment.

Next, the operation of the present embodiment will be described with reference to FIG. 12. The following description is given using a configuration example where the high-frequency treatment instrument 4C is inserted in the external tube 61.

Figure 12:
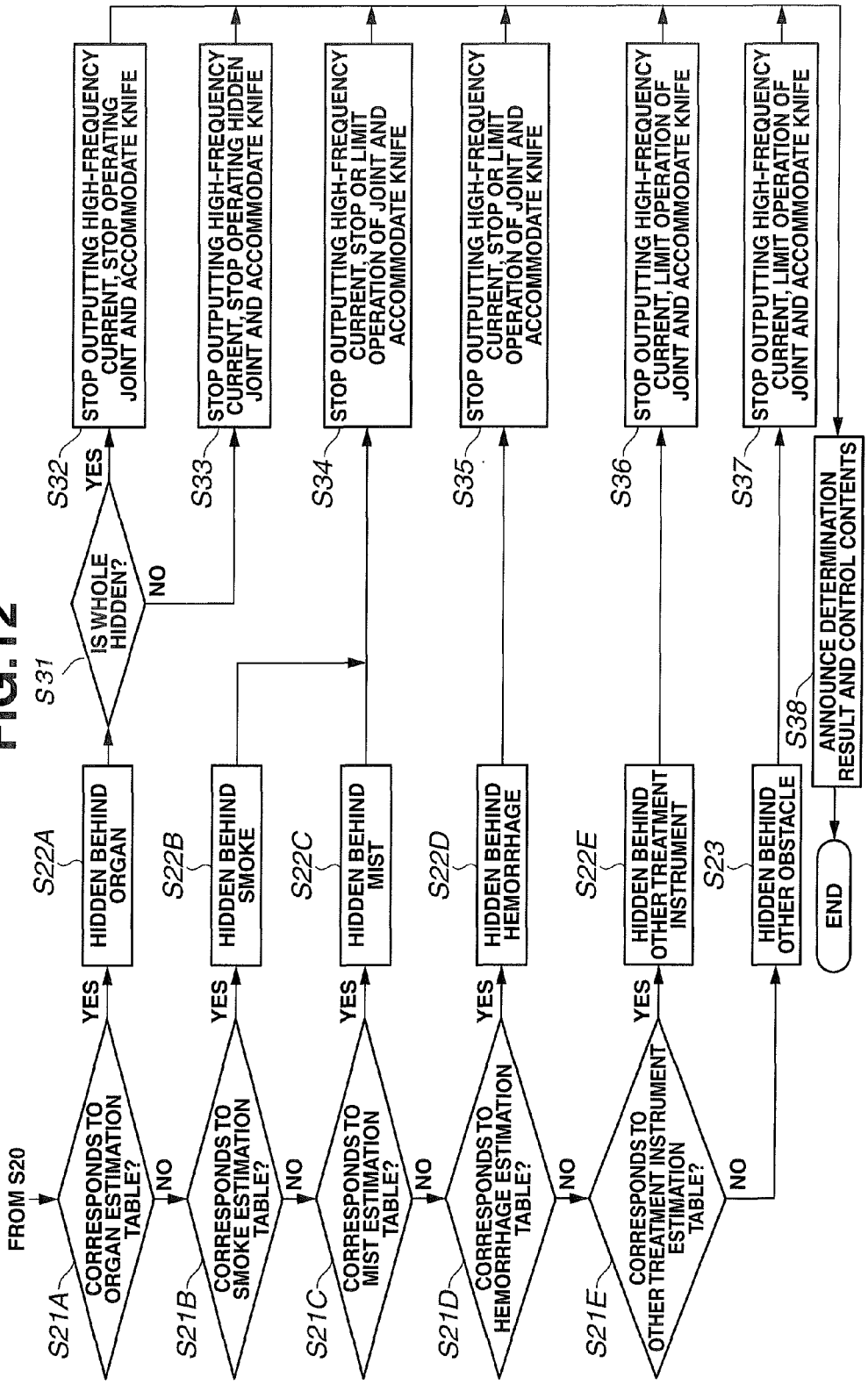
FIG. 12 is a flowchart illustrating a processing procedure for a low visibility determining method according to the third embodiment.

The present embodiment performs not only the processing in FIG. 8 described in the second embodiment but also additional processing shown in FIG. 12 through the control section 51.

As described in FIG. 8, the present embodiment performs processing of determining low visibility in step S19 and estimating an obstacle in step S20. In step S21A, the present embodiment performs processing of determining whether or not the obstacle is an organ and when the obstacle is determined to be an organ, it is determined in step S22A that the distal end portion of the high-frequency treatment instrument 4C is hidden behind the organ. Here, the distal end portion of the high-frequency treatment instrument 4C is meant to include the bending portion 52 and the treatment section 9b, but a peripheral portion of the distal end portion of the high-frequency treatment instrument 4C may be used instead of the distal end portion of the high-frequency treatment instrument 4C so as to more explicitly include the bending portion 52 and the treatment section 9b.

In next step S31, the low visibility determining section 12' determines whether the whole of the bending portion 52 and the knives making up the treatment section 9b is hidden behind the organ or part of the bending portion 52 and the knives is hidden behind the organ.

In the case of a determination result that the whole is hidden, as shown in step S32, the control section 51 instructs the high-frequency power supply apparatus 41 to stop outputting a high-frequency current.

Furthermore, the control section 51 stops the rotation operations of the joint shafts 54a and 54b making up the bending portion 52 during low visibility and also stops the rotation operation of the joint shaft 54c that opens/closes the knives. Furthermore, the control section 51 drives the motor 62 to rotate to accommodate the knives inside the distal end opening of the external tube 61.

When the determination result in step S31 shows that part is hidden, the control section 51 instructs the high-frequency power supply apparatus 41 to stop outputting (stop energy supply) a high-frequency current as shown in step S33.

The control section 51 stops the rotation operation of the hidden joint shaft and also stops the rotation operation of the joint shaft 54c that opens/closes the knives during low visibility. Furthermore, the control section 51 drives the motor 62 to rotate to accommodate the knives in the distal end opening of the external tube 61.

As shown in step S21B and step S22B or step S21C and step S22C, when it is determined that the distal end portion of the high-frequency treatment instrument 4C is hidden behind smoke or mist, the control section 51 instructs the high-frequency power supply apparatus 41 to stop outputting a high-frequency current as shown in step S34.

Furthermore, the control section 51 stops or limits (so as to reduce the response speed) the rotation operation of the joint shaft making up the bending portion 52 responsible for low visibility and also stops the rotation operation of the joint shaft 54c that opens/closes the knives. Furthermore, the control section 51 drives the motor 62 to rotate to accommodate the knives in the distal end opening of the external tube 61.

As shown in step S21D and step S22D, when it is determined that the distal end portion of the high-frequency treatment instrument 4C is hidden behind a hemorrhage, the control section 51 instructs the high-frequency power supply apparatus 41 to stop outputting a high-frequency current as shown in step S35.

Furthermore, the control section 51 stops or limits (so as to reduce the response speed) the rotation operation of the joint shaft making up the bending portion 52 responsible for low visibility and also stops the rotation operation of the joint shaft 54c that opens/closes the knives. Furthermore, the control section 51 drives the motor 62 to rotate to accommodate the knives in the distal end opening of the external tube 61.

As shown in step S21E and step S22E, when it is determined that the distal end portion of the high-frequency treatment instrument 4C is hidden behind another treatment instrument, the control section 51 instructs the high-frequency power supply apparatus 41 to stop outputting a high-frequency current as shown in step S36.

Furthermore, the control section 51 limits (so as to reduce the response speed) the rotation operation of the joint shaft making up the bending portion 52 responsible for low visibility and also stops the rotation operation of the joint shaft 54c that opens/closes the knives. Furthermore, the control section 51 drives the motor 62 to rotate to accommodate the knives in the distal end opening of the external tube 61.

As shown in step S23, when it is determined that the distal end portion of the high-frequency treatment instrument 4C is hidden behind another obstacle, the control section 51 performs the control shown, for example, in step S32 or S33, as shown in step S37. To be more specific, the control section 51 instructs the high-frequency power supply apparatus 41 to stop outputting a high-frequency current.

Furthermore, the control section 51 stops the rotation operation of the joint shaft making up the bending portion 52 responsible for low visibility and also stops the rotation operation of the joint shaft 54c that opens/closes the knives.

Furthermore, the control section 51 drives the motor 62 to rotate to accommodate the knives in the distal end opening of the external tube 61.

After the processing in steps S32 to S37, in step S38, the monitor 8 announces the determination result and control contents by the control section 51 and this processing ends.

As shown in FIG. 8, after the processing in steps S22A to S22E, if the monitor 8 makes an announcement by displaying the determination result, after the processing in steps S32 to S36, the monitor 8 may make an announcement by displaying the information on the control result by the control section 51.

Furthermore, when the obstacle is smoke or mist, it may be possible to determine to what extent contours of the treatment instrument can be recognized through image processing and change the operation controlled by the control section 51 according to the determination result.

For example, although the image becomes more unclear due to smoke or mist than when there is no smoke or mist, if the contours of the knives and the bending portion 52 can be sufficiently observed, the response operation may be slowed to enable the operation of the high-frequency treatment instrument 4C to continue.

According to the present embodiment that performs such an operation, when an active high-frequency treatment instrument 4C is used, if low visibility occurs, the operations by the high-frequency treatment instrument 4C and high-frequency power supply apparatus 41 are controlled according to the type or situation of an obstacle responsible for the low visibility, and it is thereby possible to reduce time and trouble with which the surgeon must manually operate.

Therefore, even when the surgeon has to perform a treatment in a circumference in which low visibility occurs, the surgeon can more easily perform a smooth treatment. In addition, the present embodiment has effects similar to those of the second embodiment.

When it is determined that the obstacle is smoke or mist, the present embodiment stops outputting a high-frequency current, in other words, prevents a high-frequency current from flowing into the high-frequency treatment instrument 4C and the distal end portion side thereof, and can thereby immediately stop generation of smoke or mist.

For this reason, at the initial stage at which smoke or mist occurs, the control section 51 performs control so as to stop outputting a high-frequency current, and there is a high possibility that a state in which visibility can be secured may be restored from a low visibility state.

Thus, when it is determined that the obstacle is smoke or mist, the control section 51 may suspend stopping of the output of a high-frequency current, and then limit the operation of the joint so as to slow the response speed of the operation of the joint driven by the drive section 50 in response to the instruction operation by the operation section 60 and also limit the operation so as to temporarily stop the operation of the knives or slow the response speed (not perform control of accommodating the treatment section 9b (knives) in the treatment section accommodation section as follows).

Control contents controlled by the control section 51 may be changed when it is determined that the obstacle is smoke or mist and when it is determined that the obstacle is other than smoke or mist. When it is determined that the obstacle is other than smoke or mist, the control section 51 retracts (the knives that make up) the treatment section 9b and performs control of accommodating the treatment section 9b in the distal end opening 3b of the channel 3 or in the distal end opening of the external tube 61, that is, in the accommodation section of the treatment section. Furthermore, when it is determined that the obstacle is smoke or mist, the control section 51 may slow the response speed of the operation driven by the drive section 50 or when it is determined that the obstacle is other than smoke or mist, the control section 51 may perform control so as to stop the operation driven by the drive section 50. Furthermore, when such control is performed, the control contents may be displayed on the monitor 8 or the like to make it easier for the surgeon to grasp or recognize the control contents.

Figure 13:
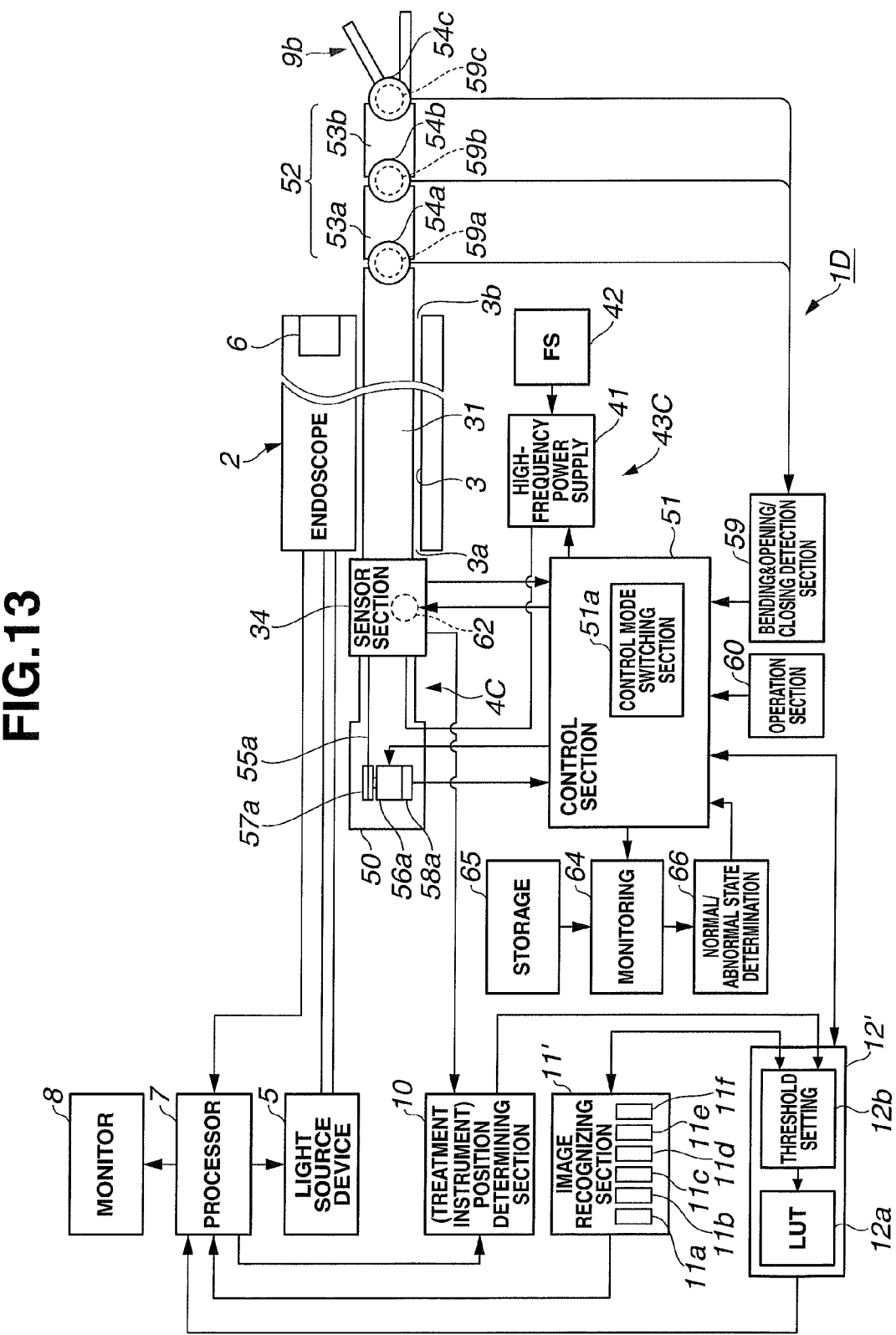
FIG. 13 is a configuration diagram illustrating an overall configuration of an endoscope system according to a modification example of the third embodiment.

FIG. 13 illustrates an overall configuration of an endoscope system 1D of a modification example. This endoscope system 1D corresponds to, for example, the endoscope system 1C according to the third embodiment shown in FIG. 10 provided with a monitoring section 64 that monitors the drive amount detected by an encoder 58i or the like of the drive section 50 and detection values of sensors 59a to 59c.

Furthermore, a storage section 65 that chronologically stores the drive amount of a drive section 50 and detection values of the sensors 59a to 59c or the like is also provided. The storage section 65 may also be configured to store a high-frequency current value or the like outputted from the high-frequency power supply apparatus 41.

The monitoring section 64 may also directly monitor the output signals of the encoder 58i and sensors 59a to 59c or may perform monitoring via the control section 51 as shown in FIG. 13. The monitoring section 64 may further monitor other operations.

Furthermore, the storage section 65 stores a drive characteristic of the drive section 50, a bending characteristic of a bending portion 52 or the like beforehand and the monitoring section 64 has a function of a normal/abnormal state determining section 66 that determines a normal state in which the drive amount monitored or detection value is within an allowable range of drive amount or detection value or an abnormal state in which the drive amount monitored or detection value deviates from the allowable range with reference to the characteristics of the storage section 65.

The determination result by the normal/abnormal state determining section 66 is sent to the control section 51. The control section 51 performs a control operation corresponding to this determination result. In the case of a normal state, the control section 51 performs a control operation as in the case of the aforementioned third embodiment.

In the case of an abnormal state, the control section 51 performs a control operation in a control mode (third control mode) corresponding to the abnormal state. In this control mode, the control section 51 stops the drive operation of the drive section 50 in which an abnormal state is detected and controls the operations of a high-frequency treatment instrument 4C and a high-frequency power supply apparatus 41 without using the detection value of the sensor in which an abnormal state is detected. Furthermore, when the abnormal state is canceled, the operation is substantially the same as that in the third embodiment (however, a monitoring operation which is not performed in the third embodiment is performed).

Information on the control mode of the control section 51 may be announced to the surgeon or the like by displaying it on the monitor 8 via the processor 7.

The rest of the configuration is similar to that of the third embodiment. According to the present modification example, even in the case of an abnormal state, a control operation corresponding to the abnormal state can be performed. The third embodiment and the modification example thereof have been described using the case with the high-frequency treatment instrument 4C, the present invention is likewise applicable to an ultrasound treatment instrument or the like.

Here, an endoscope system which will be described in FIG. 14 and subsequent figures may also be configured.

Figure 14:
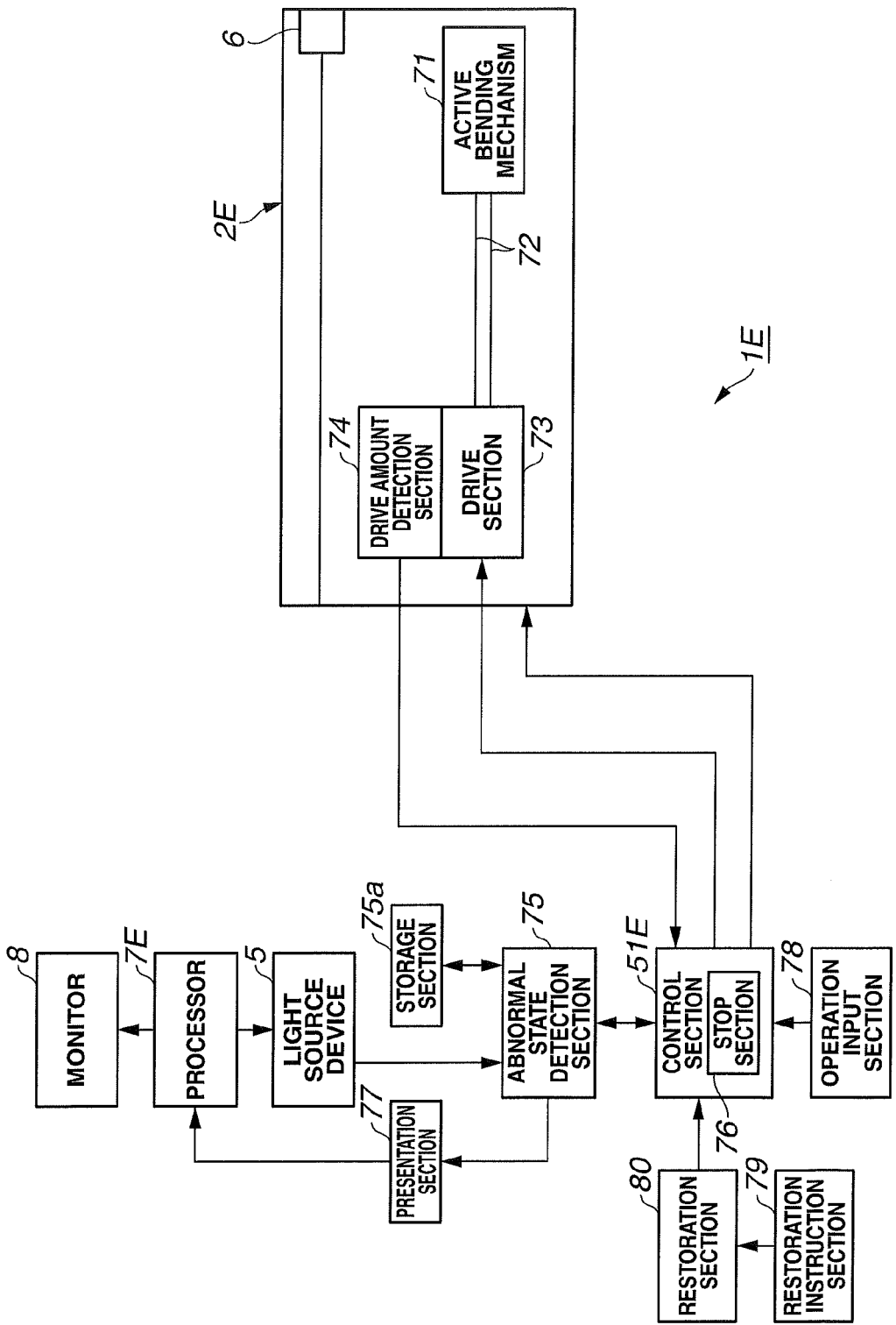
FIG. 14 is a configuration diagram illustrating an overall configuration of an endoscope system provided with an abnormal state detection section.

An endoscope system 1E shown in FIG. 14 includes an active endoscope (simply abbreviated as "endoscope") 2E as an active medical instrument, a light source device 5, a processor 7E, a monitor 8, and a control section 51E that controls the operation of the endoscope 2E.

The endoscope 2E is provided with an active bending mechanism 71 made up of a plurality of joints in the vicinity of the distal end portion and the active bending mechanism 71 is connected to a drive section 73 on the surgeon's hand side via a wire 72. The endoscope 2E corresponds to a configuration with the bending portion 18 of the endoscope 2 in FIG. 2 replaced by the active bending mechanism 71.

The operation of driving joints of the active bending mechanism 71 by the drive section 73 is controlled by the control section 51E. Furthermore, the drive amount of the drive section 73 is detected by a drive amount detection section 74 and outputted to the control section 51E.

Furthermore, an abnormal state detection section 75 that detects an abnormal state in which each section or device in the endoscope system 1E operates differently from a normal operation state due to malfunction or the like is connected to the control section. A storage section 75a stores information for detecting an abnormal state such as an operation characteristic of the drive section 73 or the like and the abnormal state detection section 75 refers to the information or the like stored in the storage section 75a.

The abnormal state detection section 75 always monitors an operation state of the endoscope 2E such as a drive state of the drive section 73 (drive torque, drive amount), amounts of displacement of joints making up the active bending mechanism 71, state of the image pickup section 6 of the endoscope 2E or operation states of the light source device 5, processor 7E, peripheral devices of the endoscope and checks whether or not functions of the devices are operating normally. The processor 7E has the same configuration of the processor 7 in FIG. 2 without the endoscope image information acquiring circuit 27, but the processor 7E may also be configured to include the endoscope image information acquiring circuit 27.

If the abnormal state detection section 75 determines that part of the above function is abnormal, for example, the abnormal state detection section 75 sends a signal indicating an abnormality to a stop section 76 provided inside the control section 51E and a presentation section 77 outside the control section 51E, the stop section 76 stops the function of the endoscope 2E, the presentation section 77 outputs an alarm to the surgeon on the monitor 8 via, for example, the processor 7E. The presentation section 77 itself may also perform an operation of outputting an alarm.

Furthermore, the endoscope system 1E includes an operation input section 78 that inputs various instruction operations to the control section 51E, a restoration instruction section (operation instruction section) 79 that gives an operation instruction of a normal function portion when an abnormal state occurs, and a restoration section (operation control section) 80 that causes, for example, the control section 51E to perform an operation of a normal function portion according to the operation instruction of the restoration instruction section 79.

In the endoscope system 1E having such a configuration, when, for example, the endoscope 2E is performing a diagnosis or treatment, if abnormality occurs in some joints and the entire function of the endoscope 2E is stopped, the diagnosis or treatment function drastically deteriorates.

Thus, the present endoscope system 1E selectively restores the image pickup section 6 as the image pickup function of the endoscope 2E using the restoration section 80, sets an operation state in which a visual function is operated and thereby facilitates a diagnosis or treatment.

Furthermore, a minimum operation is preferably performed to remove the endoscope 2E, highly reliable operations are secured even when active control is performed by selecting joints of normally operating portions or the drive section 73 that operates the joints and restoring operation of only the normal joints.

Thus, upon detecting an abnormal state, the present endoscope system 1E temporarily stops all functions, but by selectively restoring normal functions, the present endoscope system 1E can perform a minimum operation even when ending manipulation or the like, and can improve operability when handling an active medical instrument.

Figure 15:
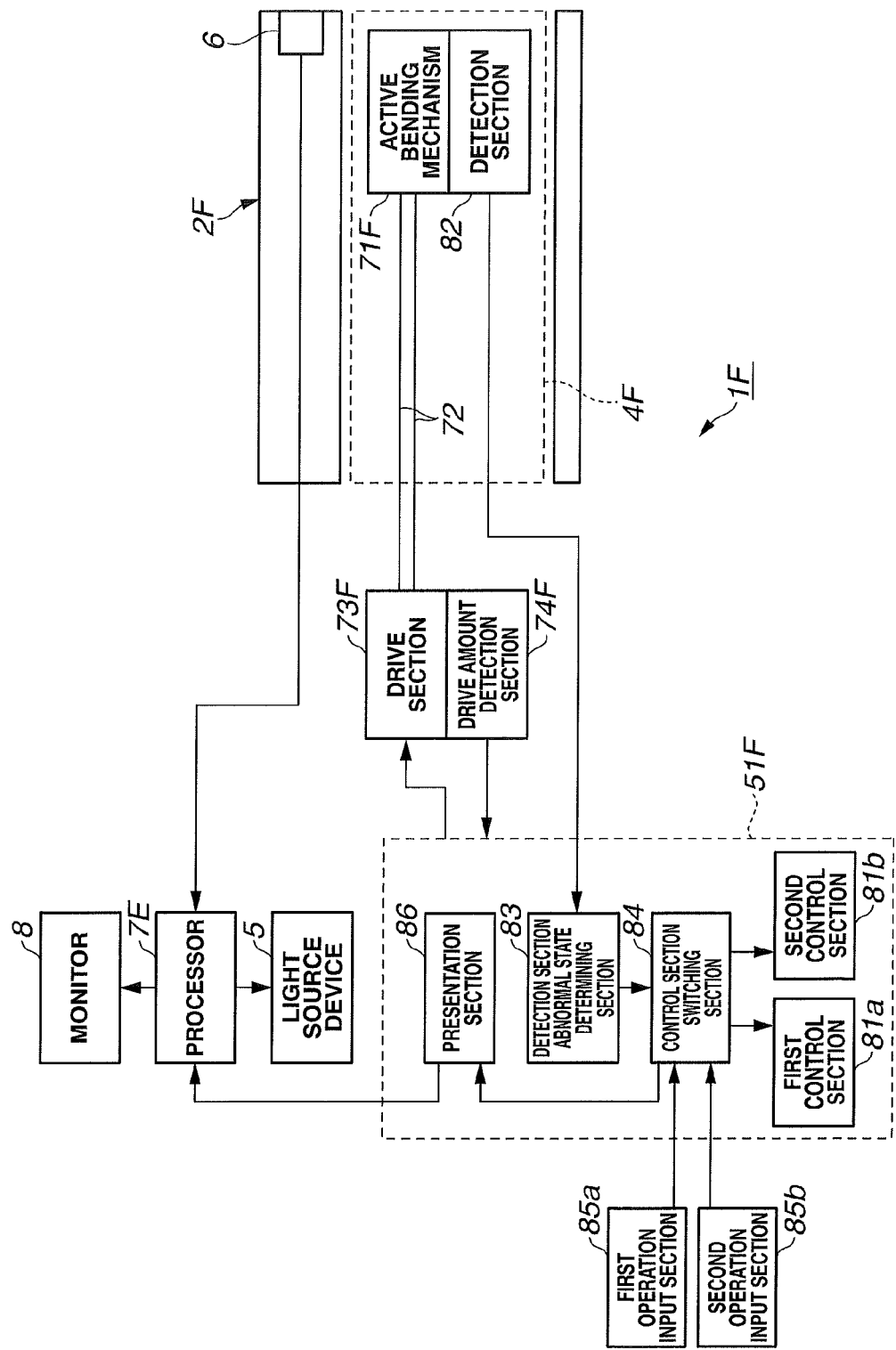
FIG. 15 is a configuration diagram illustrating an overall configuration of an endoscope system provided with first and second control sections.

An endoscope system 1F shown in FIG. 15 includes an endoscope 2F, an active treatment instrument 4F inserted in a channel of the endoscope 2F, a light source device 5, a processor 7E, a monitor 8 and a treatment instrument control section 51F provided with first and second control sections 81a and 81b that control the active treatment instrument 4F.

The active treatment instrument 4F is provided with an active bending mechanism 71F made up of a plurality of joints in the vicinity of the distal end portion and the active bending mechanism 71F is connected to a drive section 73F made up of a motor on the surgeon's hand side via a wire 72.

The operation of driving the joints of the active bending mechanism 71F by the drive section 73F is controlled by the treatment instrument control section 51F. The active bending mechanism 71F is provided with a detection section 82 made up of a sensor or the like for detecting an amount of displacement of each joint.

The drive amount of the drive section 73F is detected by a drive amount detection section 74F made up of an encoder and outputted to the treatment instrument control section 51F.

Furthermore, a signal detected by the detection section 82 is inputted to the treatment instrument control section 51F and also inputted to a detection section abnormal state determining section 83 provided inside the treatment instrument control section 51F. The detection section abnormal state determining section 83 determines (detects) an abnormal state due to a malfunction or the like of the detection section 82 provided for the active bending mechanism 71F.

During a normal operation when the detection section 82 is determined to be normally operating, the detection section abnormal state determining section 83 performs switching via the control section switching section 84 so as to use the first control section 81a for control.

In this case, the first control section 81a controls the operation of the active treatment instrument 4F based on the signal of the detection section 82.

On the other hand, in the event of abnormality when the detection section 82 is determined to be in an abnormal operation state, the detection section abnormal state determining section 83 performs switching via the control section switching section 84 so as to use the second control section 81b for control.

The second control section 81b performs a control operation that controls the respective joints making up the active bending mechanism 71F independently and controls only joints detected by sensors based on signals from the sensors that normally operate even when some of the plurality of sensors making up the detection section 82 malfunction.

Furthermore, the control section switching section 84 is connected to a first operation input section 85a and a second operation input section 85*b* that input instructions to the first control sections 81*a* and 81*b*. Furthermore, the treatment instrument control section 51F is provided with a presentation section 86 for presenting the state of the treatment instrument control section 51F to the surgeon.

The control method in such an endoscope system 1F will be described. In general, when part of a device malfunctions while controlling an active medical instrument, a treatment or the like is stopped and the active medical instrument is removed from within the body, but in the case of a multi-degree-of-freedom active treatment instrument 4F, if a malfunction or the like occurs when each joint has a large bent shape, it may be difficult to remove the active treatment instrument 4F from within the body.

Furthermore, when a treatment is in progress, it is necessary to perform a minimum degree of treatment and complete the manipulation. The present endoscope system 1F provides a method of controlling the active treatment instrument 4F focusing on such a case.

First, the method of controlling the active treatment instrument 4F in a normal operation will be described. In a normal operation, control is performed using the first operation input section 85*a* and the first control section 81*a*. The detection section abnormal state determining section 83 mounted on the treatment instrument control section 51F determines whether the detection value is normal or abnormal every time it acquires a detection value from the detection section 82.

Examples of main determining method employed include a method of determining an abnormality (malfunction) when no detection value can be acquired due to wire breakage or physical damage or a method of determining an abnormality when a detection value becomes an electrically or thermally abnormal value such as noise and by further acquiring such abnormal values consecutively. Temporary false detection can be coped with using a filter or the like.

The method of controlling the first control section 81*a* is a method of controlling the position or posture of the distal end portion of the active treatment instrument 4F and the surgeon inputs a desired position or posture using the first operation input section 85*a*.

The first control section 81*a* then calculates a bending angle of each joint based on an input value and controls the amount of rotation of the motor making up the drive section 73F according to the calculation result. Use of this method makes it possible to intuitively operate a multi-degree-of-freedom active treatment instrument.

Here, when a sensor set up in a certain sensor malfunctions, the detection section abnormal state determining section 83 determines it as an abnormality, sends a signal indicating the abnormal state to the control section switching section 84 and the presentation section 86 and the control section switching section 84 sends a signal indicating that the sensor is in an abnormal state to the first and second control sections 81*a* and 81*b*.

At this time, the first control section 81*a* stops the operation of the active treatment instrument 4F until each device starts the next action and does not allow input from the first operation input section 85*a*. The presentation section 86 presents a signal indicating that the sensor malfunctions to the surgeon on the monitor 8 via the processor 7E. Alarming means such as voice in addition to a display may be used for the presentation method.

After presenting the information to the surgeon, the control section switching section 84 switches from the first control section 81*a* to the second control section 81*b* so as to perform a control operation, sends a signal to the presentation section 86 indicating that the input operation is switched from the first operation input section 85*a* to the second operation input section 85*b* and the presentation section 86 presents the information to the surgeon.

Switching of the control section may also be performed using a method according to a switching instruction from the surgeon. Furthermore, instead of providing two operation input sections, a plurality of input modes may be provided on one operation input section and switching may be performed between these modes.

When the surgeon starts an operation input instruction from the second operation input section 85*b*, the second control section 81*b* starts controlling the active treatment instrument 4F. As described above, the method of controlling the second control section 81*b* is a method of controlling the respective joints of the active treatment instrument 4F independently and when sensors of some joints malfunction, it is possible to control only joints whose sensors operate normally.

When all the sensors malfunction, a control method using values of encoders making up the drive amount detection section 74F may also be used.

Using the above methods, when a sensor mounted at the distal end portion malfunctions, the active treatment instrument 4F can be controlled.

Figure 16:
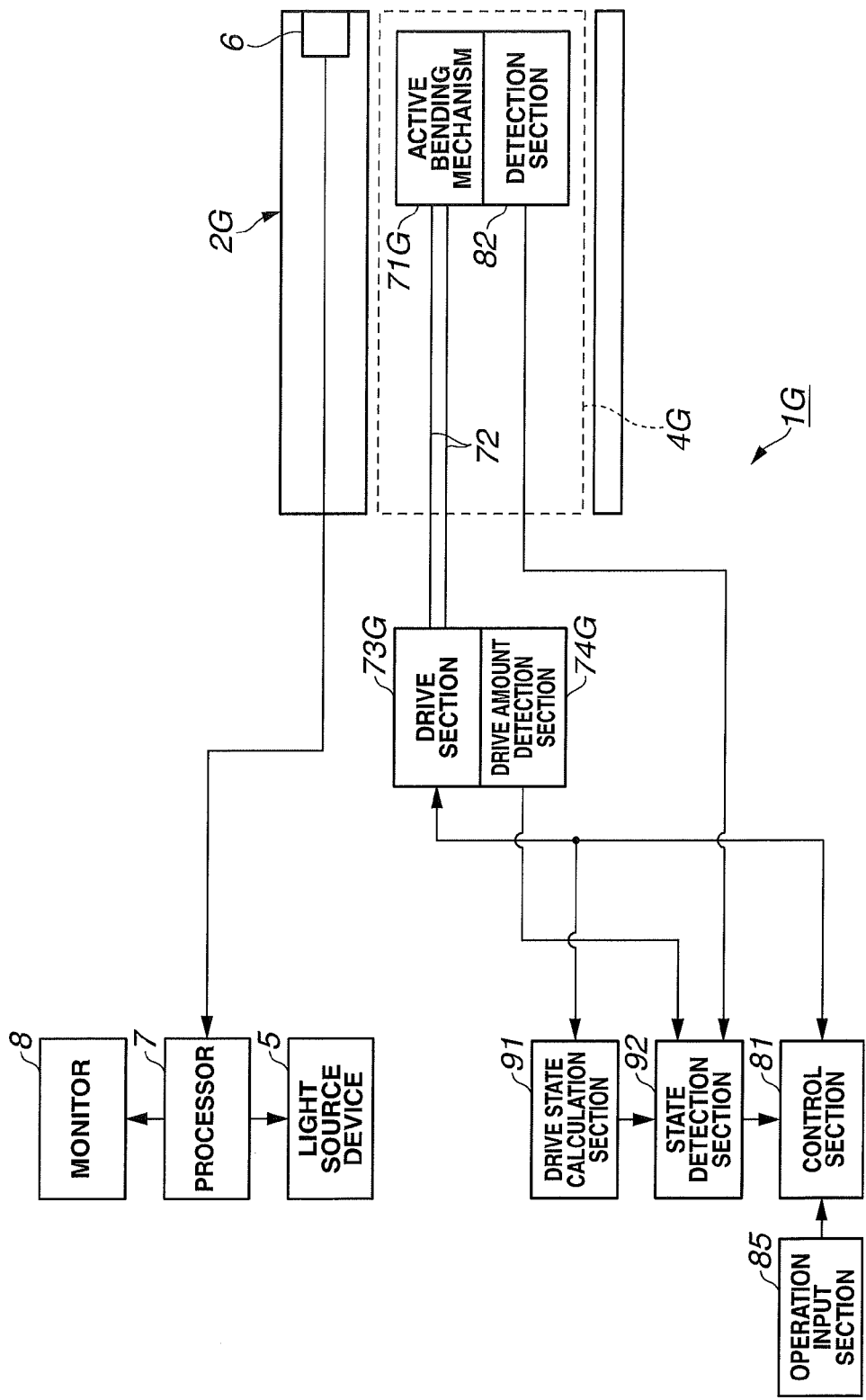
FIG. 16 is a configuration diagram illustrating an overall configuration of an endoscope system provided with a state detection section.

An endoscope system 1G shown in FIG. 16 may also be adopted, which is a partially modified version of the configuration of the endoscope system 1F in FIG. 15.

In this endoscope system 1G, the drive section 73F in the endoscope system 1F in FIG. 15 is controlled by a control section 81. Furthermore, the drive section 73F is connected to a drive state calculation section 91 that calculates the drive output as a drive state of this drive section 73F. The drive amount detection section 74F and the detection section 82 are connected to a state detection section 92. The control section 81 is connected to an operation input section 85.

This endoscope system 1G detects wire breakage of the active treatment instrument 4F or an external force applied to the distal end portion, predicts a motor malfunction using detection values of sensors making up the detection section 82 mounted at the distal end portion of the active treatment instrument 4F and controls the active treatment instrument 4F according to the detection results.

The control section 81 controls the active treatment instrument 4F based on the sensor information provided at each joint. Performing motor control using detection values of the encoders can also improve the accuracy.

Next, the method of detecting the state of the active treatment instrument 4F will be described using FIG. 17. For an input of the operation input section 85 as shown in step S41, the motor of the drive section 73F operates based on the input value (step S42). The drive amount detection section 74F acquires an encoder value corresponding to the drive amount of the motor (step S43).

Furthermore, when the motor operates, the drive state calculation section 91 calculates the output torque of the motor and compares it with the output torque during a normal operation of the active treatment instrument 4F, that is, an appropriate output torque value (step S44).

When the output torque is greater than that during the normal operation, the state detection section 92 detects that the load imposed on the motor is large (to be more specific, if this load state continues, the motor may be damaged) (step S45).

Upon detecting the aforementioned two states, the state detection section 92 sends a signal indicating the aforementioned states to the control section 81, the control section 81 predicts a burnout of the motor and limits the output to the motor (drive section) (step S46). Examples of the limitation method include torque control, current control or voltage control.

Furthermore, the state detection section 92 detects the following two states.

A first state is a state in which the distal end portion of the active treatment instrument 4F is in contact with an organ or the like in the body and a burden is imposed on the operation of the active treatment instrument 4F and a second state is a state in which a burden is imposed on the insertion section of the active treatment instrument 4F interposed between the motor and joints.

These states are determined by the state detection section 92 by comparing the detection value of the sensor provided at the joint with the amount of rotation of the motor. The state detection section 92 then determines whether or not the detection value of the distal end portion is appropriate (step S47).

When the determination result shows that the detection value is not appropriate, the state detection section 92 determines (detects) that a burden is imposed on the insertion portion (step S48). On the other hand, when the determination result shows that the detection value is appropriate, the state detection section 92 determines that an external force is received in the operation state (step S49).

Furthermore, when the determination result in above step S44 shows that the output torque value is appropriate, the state detection section 92 determines whether or not the sensor can acquire the detection value (sensor value) of the distal end portion (step S50).

When the state detection section 92 cannot normally acquire the sensor value of the distal end portion, the state detection section 92 determines a malfunction of the sensor or wire breakage (step S51). Furthermore, the state detection section 92 sends a signal indicating this state to the control section 81.

Upon receiving the above signal, the control section 81 stops or limits the output of the motor.

In addition to stoppage or limitation, the control method in the event of a malfunction of the sensor may also be switching between different control blocks without using the value of the sensor at the distal end portion such as control using the amount of rotation of the motor.

Furthermore, such a determination is also made when acquiring a detection value of the sensor at the distal end portion at the time of predicting a burnout of the motor.

When determining that the value detected by the detection section has been normally acquired, the state detection section 92 determines whether or not the acquired detection value is appropriate (step S52). The determination is made by a comparison with the detection value of the previous state or a comparison with the other sensor.

When the detection value is appropriate, the state detection section 92 determines that the active treatment instrument 4F is operating normally and continues the control (step S53).

On the other hand, when determining that the detection value is not appropriate, the state detection section 92 detects the following three states according to the detection result and sends the detection result to the control section 81.

First, although the amount of rotation of the motor is detected, if the detection result of the detection section 82 does not change, the state detection section 92 determines that a wire breakage has occurred since power is not transmitted to the joint at the distal end portion (step S54).

Next, when the detection result of the detection section 82 is a value irrelevant to operation of the joints of the active treatment instrument 4F and these values are consecutively acquired, the state detection section 92 determines that the sensor is electrically malfunctioning (step S55).

Finally, although the driven motor or the joint maintains an input state in response to the inputted position or posture, if the detection value of the joint then changes, the state detection section 92 determines that the joint at the distal end portion is receiving an external force such as pressure from an organ or the like (step S56).

Upon receiving such state signals, the control section 81 performs the following control.
(Upon detecting wire breakage) The control section 81 stops the operation of the motor or operates only the joint whose wire is not broken.
(In event of sensor malfunction) The control section 81 stops the operation of the motor.
(Upon detecting external force) The control section 81 limits the output of the motor.

As described above, by not only detecting a sensor malfunction but also detecting, in a controlled manner, the presence or absence of influences of a wire breakage or external force, which is conventionally recognized by the surgeon, it is possible to improve reliability in the control of the active treatment instrument 4F, reduce time and trouble of operations by the surgeon or the like and thereby improve operability.

The endoscope system 1G shown in FIG. 16 may also be configured so as to allow the active treatment instrument 4F (or treatment manipulator) to communicate with other devices and detect normal/abnormal states of the active treatment instrument 4F and other devices so that the control section 81 may perform control corresponding to the normal/abnormal states.

Furthermore, in this case, a configuration including the processor 7 (or an imaging apparatus), an energy device such as high-frequency treatment instrument and an insufflator as the other devices may be adopted. Depending on each device in which an abnormal state is detected as shown in FIG. 18, the control section 81 may control the operation such as stopping or temporarily stopping or continuing the operation of each device making up the endoscope system.

With such control, even when an abnormal state occurs during a surgery, it will be easier to make an appropriate setting corresponding to the abnormal state and smoothly perform an appropriate operation as a whole.

An embodiment configured by partially combining the aforementioned embodiments or the like also belongs to the present invention. Furthermore, modification examples without departing from the scope and spirit of the present invention also belong to the present invention.

What is claimed is:

1. An endoscope system comprising:
an image pickup section, provided in an endoscope, which performs image pickup;
a determining section that determines whether or not a specific observation object exists inside an image pickup region of the image pickup section;
a recognizing section that determines whether or not the specific observation object can be recognized as an image from the picked-up image in the image pickup region picked up by the image pickup section;
a low visibility determination output section that determines, when the determining section determines that the specific observation object exists inside the image pickup region and the recognizing section cannot recognize the specific observation object as an image, that the image pickup section is in a low visibility condition and outputs a low visibility determination result; and an obstacle estimation section that estimates an obstacle or a type of obstacle which causes the low visibility according to the low visibility determination result.

2. The endoscope system according to claim 1, wherein the specific observation object is a distal end portion of a treatment instrument, and when part of the distal end portion of the treatment instrument cannot be recognized as an image, the low visibility determination output section determines that the image pickup section is in a low visibility condition.

3. The endoscope system according to claim 2, further comprising a control section that controls operation of the treatment instrument, wherein the control section performs control so as to stop or limit the operation of the treatment instrument according to an obstacle or a type of obstacle estimated by the obstacle estimation section.

4. The endoscope system according to claim 3, wherein the specific observation object is a distal end portion of an active treatment instrument, a plurality of joints of which are rotated by a drive section, and the control section that controls the operation of the treatment instrument further comprises a second control section that controls operation of the drive section in the active treatment instrument.

5. The endoscope system according to claim 4, wherein when the active treatment instrument performs a treatment using energy supplied from an energy supply apparatus, the control section performs control so as to stop or limit operation of the drive section in the active treatment instrument and also stop operation of energy supply by the energy supply apparatus according to an obstacle or a type of obstacle estimated by the obstacle estimation section.

6. The endoscope system according to claim 5, wherein the control section changes contents of control on the active treatment instrument between when the obstacle is estimated to be smoke or mist and when the obstacle is estimated to be other than smoke or mist.

7. The endoscope system according to claim 5, wherein when the obstacle is estimated to be smoke or mist, the control section controls the active treatment instrument so as to slow the response speed of the operation of the drive section of driving in response to an instruction operation and controls the active treatment instrument, when the obstacle is estimated to be other than smoke or mist, so as to stop the operation of driving of the drive section.

8. The endoscope system according to claim 5, wherein when the obstacle is estimated to be smoke or mist, the control section controls the active treatment instrument so as to slow the response speed of the operation of driving a treatment section provided at a distal end of the active treatment instrument for performing a treatment and controls, when the obstacle is estimated to be other than smoke or mist, the active treatment instrument so as to stop the operation of the treatment section and retract the treatment section to accommodate the treatment section inside a treatment section accommodation section.

9. The endoscope system according to claim 1, further comprising an announcing section that announces the low visibility determination result by the low visibility determination output section or information on an obstacle or a type of obstacle estimated by the obstacle estimation section.

10. An operation method of a low visibility determining system, comprising:

a display step of displaying an image of a site to be observed in a body cavity picked up by an image pickup section as an endoscope image;

a treatment instrument position acquiring step of a position determining section acquiring a position of a distal end portion of a treatment instrument for conducting a treatment of the site to be observed;

a position determining step of the position determining section determining whether or not the distal end portion of the treatment instrument is located inside an image pickup region as a region of the picked-up image;

a recognizing step of an image recognizing section conducting image recognition as to whether or not the distal end portion of the treatment instrument can be recognized as an image of an interior of the image pickup region through image processing on the picked-up image;

a low visibility determination outputting step of a low visibility determining section determining low visibility when the distal end portion of the treatment instrument is determined in the position determining step to be inside the image pickup region and the recognition result in the recognizing step shows that the distal end side of the treatment instrument cannot be recognized as an image inside the image pickup region and outputting a low visibility determination result; and an obstacle estimating step of an obstacle estimation section estimating, when the low visibility determination result is outputted in the low visibility determination outputting step, an obstacle or a type of obstacle that causes the low visibility.

\* \* \* \* \*